US006171596B1

(12) United States Patent
Earl et al.

(10) Patent No.: US 6,171,596 B1
(45) Date of Patent: Jan. 9, 2001

(54) OLIGOMERIC HIV-1 ENVELOPE GLYCOPROTEINS

(75) Inventors: Patricia L. Earl, ChevyChase; Christopher C. Broder, Rockville, both of MD (US); Robert W. Doms, Berwyn, PA (US); Bernard Moss, Bethesda, MD (US)

(73) Assignee: The United States of America as represented by the Department of Health and Human Services, Washington, DC (US)

( * ) Notice: Under 35 U.S.C. 154(b), the term of this patent shall be extended for 0 days.

(21) Appl. No.: 09/070,291

(22) Filed: Apr. 30, 1998

Related U.S. Application Data

(60) Continuation-in-part of application No. 08/805,889, filed on Mar. 3, 1997, now Pat. No. 6,039,957, which is a division of application No. 08/165,314, filed on Dec. 10, 1993, now abandoned.

(51) Int. Cl.[7] .......................... A61K 39/21; A61K 39/12; C07K 16/00

(52) U.S. Cl. .................................... 424/208.1; 424/188.1; 424/199.1; 530/388.35; 530/389.4

(58) Field of Search ............................. 424/188.1, 208.1, 424/199.1; 530/388.35, 389.4

(56) References Cited

U.S. PATENT DOCUMENTS 4,725,669 2/1988 Essex et al. ......................... 530/322
6,039,957 3/2000 Earl et al. ............................ 424/208

FOREIGN PATENT DOCUMENTS 9206113 4/1992 (WO) .

OTHER PUBLICATIONS

Folding, Interaction with GRP78–BiP, Assembly and Transport of the Human Immunodeficiency Virus Type 1 Envelope Protein, Earl, Et al., Journal of Virology, Apr. 1991, pp. 2047–2055.

Multimeric CD4 Binding Exhibited by Human and Simian Immunodeficiency Virus Envelope Protein Dimers, Earl, et al., Journal of Virology, Sep. 1992, pp. 5610–5614.

Native Oligomeric Human Immunodeficiency Virus Type 1 Envelope Glycoprotein Elicits Diverse Monoclonal Antibody Reactivities, Earl, et al., Journal of Virology, May 1994, pp. 3015–3026.

Antigenic implications of human immunodeficiency virus type 1 envelope quaternary structure: Oligomer–specific and – sensitive monoclonal antibodies, Earl, et al., Proc. Natl. Acad. Sci. USA vol. 91, pp. 11699–11703, Nov. 1994, Medical Sciences.

Berman, et al. (1989) Expression and Immunogenicity of the extracellular domain of the human immunodeficiency virus type 1 envelope glycoprotein, gp 160. Journal of Virology 3489–3498.

(List continued on next page.)

*Primary Examiner*—Hankyel Park
(74) *Attorney, Agent, or Firm*—Knobbe, Martens, Olson & Bear, LLP

(57) ABSTRACT

Immunogenic compositions and methods of stimulating an immune response against the envelope protein of HIV-1. Immunogenic compositions include a purified oligomeric structure that comprises a C-terminally truncated form of HIV-1 gp160 protein that is missing the gp41 transmembrane domain. The gp120-gp41 proteolytic processing site is retained in one form of the composition and is deleted in a different form of the composition. In one embodiment, the engineered env protein is proteolytically cleaved, but the gp120 and gp41 components of the complex remain noncovalently associated. Immunization with these compositions advantageously stimulates the production of conformation-dependent antibodies.

5 Claims, 4 Drawing Sheets

OTHER PUBLICATIONS

Earl, et al. (1992) Multimeric CD4 binding exhibited by human and simian immunodeficiency virus envelope protein dimers. Joural of Virology 5610–5614.

Kieny, et al. (1988) Improved antigenicity of the HIV env protein by cleavage site removal. Protein Engineering 2(3):219–225.

Marasco, et al. Design, intracellular expression, and the activity of a human anti–human immunodeficiency virus type 1 gp120 single–chain antibody. Proc. Natl. Acad. Sci. 90:7889–7893.

Nakamura, et al. (1992) Monoclonal antibodies to the extracellular domain of HIV–1 IIIB gp160 that neutralize infectivity, block binding to CD4, and react with diverse isolates. Aids Research and Human Retroviruses 8(11).

Pasquali, et al. (1990) Immunogenicity and epitope mapping of a recombinant soluble gp160 of the human immunodeficiency virus type 1 envelope glycoprotein. Aids Research and Human Retroviruses 6(9).

Steimer, et al. (1991) Neutralization of divergent HIV–1 isolates by conformation–dependent human antibodies to gp120. Science 254:105–108.

Seaver, S. (1994) Monoclonal antibodies in industry: more difficult than originally thought. Gen. Eng. News pp. 10, 21.

Earl et al., *Proc. Natl. Acad. Sci–USA* 87:648–652, Jan. 1990.

Earl et al., *J. Viroli* 65(i): 31–41, Jan. 1991.

Galfre et al., Meth Enzymol 73: 3–46, 1981.

Berman, Phillip W., et al.; Protection of chimpanzees from infection by HIV–1 after vaccination with recombinant glycoprotein gp120 but not gp160: Nature, vol. 345; Jun. 14, 1990; pp. 622–625.

Greene, Warner C.; AIDS and the Immune System; Life, Death and the Immune System; Scientific American, Sep. 1993; pp. 97–105.

Moore, John P.; Primary Isolates of Human Immunodeficiency Virus Type 1 Are Relatively Resistant to Neutrlization by Monoclonal Antibodies to gp120, and Their Neutralization Is Not Predicted by Studies with Monomeric gp120; Jounal of Virology; Jan. 1995; pp. 101–109.

Li, John; Infection of Cynomolgus Monkeys with a Chimeric HIV–1/SIV mac Virus That Expresses the HIV–1 Envelope Glycoproteins; Journal of Acquired Immune Deficiency Syndromes; 1992; pp. 639–646.

Reiman, Keith A.; An env Gene Derived from a Primary Human Immunodefieciency Virus Type 1 Isolate Confers High In Vivo Replicative Capacity to a chimeric Simian/Human Immunodeficiency Virus in Rhesus Monkeys; Journal of Virology; May 1996; pp. 3198–3206.

Pialoux, Gilles; A Prime–Boost Approach to HIV Prevenive Vacine Using a Recombinant Carnarypox Virus Expressing Glycoprotein 160 (MN) followed by a Recombinant Glycoprotein 160 (MN/LAI): AIDS Reseach and Human Retroviruses; vol. 11, No. 3; 1995; pp. 373–3142.

Berman, Phillip W.; Expression of Membrane–Associated and Secreted Variants of gp160 of Human Immunodeficiency Virus Type 1 In Vitro and in Continuous Cell Lines; Journal of Virology; Sep. 1988; pp. 3135–3142.

VanCott, Thomas C.; Antibodies with Specificity to Native gp120 and Neutralization Activity against Primary Human Immunodeficiency Virus Type 1 Isolates Elicited by Immunization with Oligomeric gp160; Journal of Virology; Jun. 1997; pp. 4319–4330.

```
                              SEQUENCE LISTING


(1) GENERAL INFORMATION:

   (iii) NUMBER OF SEQUENCES: 10


(2) INFORMATION FOR SEQ ID NO:1:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO:1:

AACATTACAC AAGCTTAATA CACTC                                               25


(2) INFORMATION FOR SEQ ID NO:2:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO:2:

CCCCCGCGGT TATTATTTTA TATACCACAG CCAATTTGT                                39


(2) INFORMATION FOR SEQ ID NO:3:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO:3:

GTGCTAAGGA TCCGTTCACT AATCG                                               25


(2) INFORMATION FOR SEQ ID NO:4:

     (i) SEQUENCE CHARACTERISTICS:
          (A) LENGTH: 39 base pairs
          (B) TYPE: nucleic acid
```

-continued (C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

TAATAACCGC GGGGGTTATT CATAATGATA GTAGGAGGC 39

(2) INFORMATION FOR SEQ ID NO:5:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Cys Asn Thr Arg Lys Ser Ile Arg Ile Gln Arg Gly Pro Gly Arg Ala
1 5 10 15

Phe Val Thr Ile Gly Lys
20

(2) INFORMATION FOR SEQ ID NO:6:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Tyr Asn Lys Arg Lys Arg Ile His Ile Gly Pro Gly Arg Ala Phe Tyr
1 5 10 15

Thr Thr Lys Asn Ile Ile Gly
20

(2) INFORMATION FOR SEQ ID NO:7:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

AATTCGCGCC ATATGAGAGT AAAGGAGACA CAGATGAATT GG 42

-continued

```
(2) INFORMATION FOR SEQ ID NO:8:

     (i) SEQUENCE CHARACTERISTICS:
          (A) LENGTH: 37 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:8:

CCAATTCATC TGTGTCTCCT TTACTTCATA TGGCGCG                                  37


(2) INFORMATION FOR SEQ ID NO:9:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:9:

CAGCATCTGT TGCAACTCAC AGTCTGGGGC                                          30


(2) INFORMATION FOR SEQ ID NO:10:

     (i) SEQUENCE CHARACTERISTICS:
          (A) LENGTH: 56 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:10:

CGCGGCTTGG TCGACGCCTT ATTTTATATA CCACAGCCAC TTTGTTATGT CAAACC             56
```

OLIGOMERIC HIV-1 ENVELOPE GLYCOPROTEINS

RELATED APPLICATIONS

The present application is a continuation-in-part of U.S. application Ser. No. 08/805,889, filed Mar. 3, 1997, now U.S. Pat. No. 6,039,957 which is a divisional of U.S. application Ser. No. 08/165,314, filed Dec. 10, 1993 now abandoned. The disclosures of these previous applications are hereby incorporated herein in their entirety by this reference thereto.

FIELD OF THE INVENTION

The present invention relates to the use of recombinant proteins to stimulate an immune response in a mammal. Specifically, the present invention describes methods for producing and purifying genetically engineered HIV-1 gp140, 140(prime) and gp120/20 glycoprotein oligomers that can be used as immunogens.

BACKGROUND OF THE INVENTION

The HIV-1 envelope (env) glycoprotein is a structurally complex integral membrane protein that targets the virus to CD4 positive cells and mediates the fusion between the viral envelope and the cellular membrane. This glycoprotein also harbors antigenic determinants that are recognized by neutralizing antibodies.

The two recognized categories of antibodies that are capable of neutralizing HIV-1 infection include: those that recognize determinants in the V3 loop of gp120 and those that block the gp120-CD4 interaction by binding to conserved regions of gp120. Antibodies directed against the V3 loop generally recognize epitopes formed by a short continuous sequence and are usually referred to as conformation-independent. These conformation-independent antibodies can be elicited by immunization with either peptides or denatured env protein subunits. Extensive antigenic variation in the V3 domain of the env protein restricts the neutralizing activity of anti-V3 loop antibodies to closely related strains of HIV-1. Hence, antibodies capable of neutralizing infection by one strain of HIV-1 may not effectively neutralize infection by a different strain of HIV-1.

In contrast, antibodies to epitopes that are sensitive to the conformation of the protein are typically more broadly neutralizing. Antibodies to these conformation-sensitive epitopes are referred to herein as "conformation-dependent" antibodies. Conformation-dependent antibodies that block CD4 binding, for example, recognize conserved, discontinuous, conformational epitopes in gp120. These antibodies are broadly neutralizing and have been shown to comprise a significant fraction of the total neutralization activity present in HIV-1 infected human sera. In addition, there is evidence that neutralizing antibodies may also be directed against conformationally-dependent epitopes on gp120 (Steimer et al., *Science,* 254:105 (1991)).

Newly synthesized gp160 monomers noncovalently associate to form higher order oligomeric structures. The association of two env monomers to form a dimer is the most elemental such structure. A larger structure that is believed to be composed of a dimer of dimers, or four monomers, can also form. The ectodomain of gp41 is required for efficient oligomerization of dimers and tetramers (Earl et al., *Proc. Natl. Acad. Sci. USA* 87:648 (1990); Earl and Moss, *AIDS Res.* 9:589–594 (1993)).

Given its antigenic nature, the use of recombinant gp160 or derivatives thereof as immunogens represents an attractive vaccine strategy. However, the attempts that have been made to date in this regard have all suffered one or another deficiency. To the extent that humoral immune responses against various gp160 immunogens have been analyzed, none satisfactorily stimulates the broadly neutralizing antibodies that would be required of an effective HIV-1 vaccine. Hence, there remains a need for a vaccine composition that can stimulate the production of broadly neutralizing antibodies against various strains of HIV-1.

SUMMARY OF THE INVENTION

In a first aspect of the invention, there is provided a composition for stimulating an anti-HIV-1 env immune response in a mammal. The composition includes an oligomer of a secreted C-terminally truncated form of an HIV-1 gp160 and a pharmaceutically acceptable carrier. The secreted C-terminally truncated form of an HIV-1 gp160 includes a gp120-gp41 proteolytic processing site. According to one embodiment the HIV-1 gp160 is found in a laboratory-adapted strain of HIV-1, such as BH8. According to another embodiment the HIV-1 gp160 is found in a primary isolate of HIV-1, such as HIV-1 89.6 or HIV-1 CM235. When the secreted C-terminally truncated form of the HIV-1 gp160 includes a gp120-gp41 proteolytic processing site, the pharmaceutically acceptable carrier can include a saline solution, and additionally may include an adjuvant. According to yet another embodiment of the invention, the secreted C-terminally truncated form of the HIV-1 gp160 can include the entire amino acid sequence of gp120 of the HIV-1.

In a second aspect of the invention, there is provided another composition for stimulating an anti-HIV-1 env immune response in a mammal. This composition includes an oligomeric gp120/20, which is a proteolytically cleaved form of a secreted C-terminally truncated form of an HIV-1 gp160, and a pharmaceutically acceptable carrier. In one embodiment the HIV-1 gp160 of the composition is found in a primary isolate of HIV-1, and the oligomeric gp120/20 has a molecular weight of at least 200 kDa.

In a third aspect of the invention, there is provided a method of stimulating the formation of neutralizing antibodies against conformational epitopes of HIV-1 env proteins in a mammal. This method includes the steps of first identifying a mammal at risk of contracting an HIV infection; and then administering to the mammal a composition which includes an oligomer of gp140(prime) and a pharmaceutically acceptable carrier, wherein the gp140(prime) is a C-terminally truncated form of an HIV-1 gp160, and the HIV-1 gp160 has a gp120-gp41 proteolytic processing site. According to one embodiment of the method, the composition is administered intramuscularly and can be administered intramuscularly a plurality of times. According to another embodiment, the HIV-1 gp160 is found in a laboratory-adapted strain of HIV-1, such as HIV-1 BH8. According to still another embodiment of the invention, the HIV-1 gp160 is found in a primary isolate of HIV-1, such as HIV-1 89.6 or HIV-1 CM235. According to yet another embodiment, the C-terminally truncated form of the HIV-1 gp160 includes the entire sequence of a mature gp120 that does not include a signal peptide.

In a fourth aspect of the invention, there is provided a recombinant oligomeric gp140.

In a fifth aspect of the invention, there is provided a recombinant oligomeric gp140(prime).

In a sixth aspect of the invention, there is provided a recombinant oligomeric gp120/20.

In a seventh aspect of the invention, there is provided a recombinant oligomeric gp140 or gp140(prime) having been produced by a two-step purification process.

In an eighth aspect of the invention, there is provided a vaccine which includes oligomeric gp140, gp140(prime) or gp120/20.

In a ninth aspect of the invention, there is provided a method of preventing HIV infection in a subject. This method includes the steps of administering a vaccine which includes oligomeric gp140, gp140(prime) or gp120/20 in an amount sufficient to prevent HIV infection.

In a tenth aspect of the invention, there is provided the recombinant viral construct vPE12B.

In an eleventh aspect of the invention, there is provided the plasmid construct pPE12B.

In a twelfth aspect of the invention, there is provided the recombinant viral construct vCB-14.

In a thirteenth aspect of the invention, there is provided the plasmid construct pCB-14.

DETAILED DESCRIPTION OF THE INVENTION

Figure 1A:
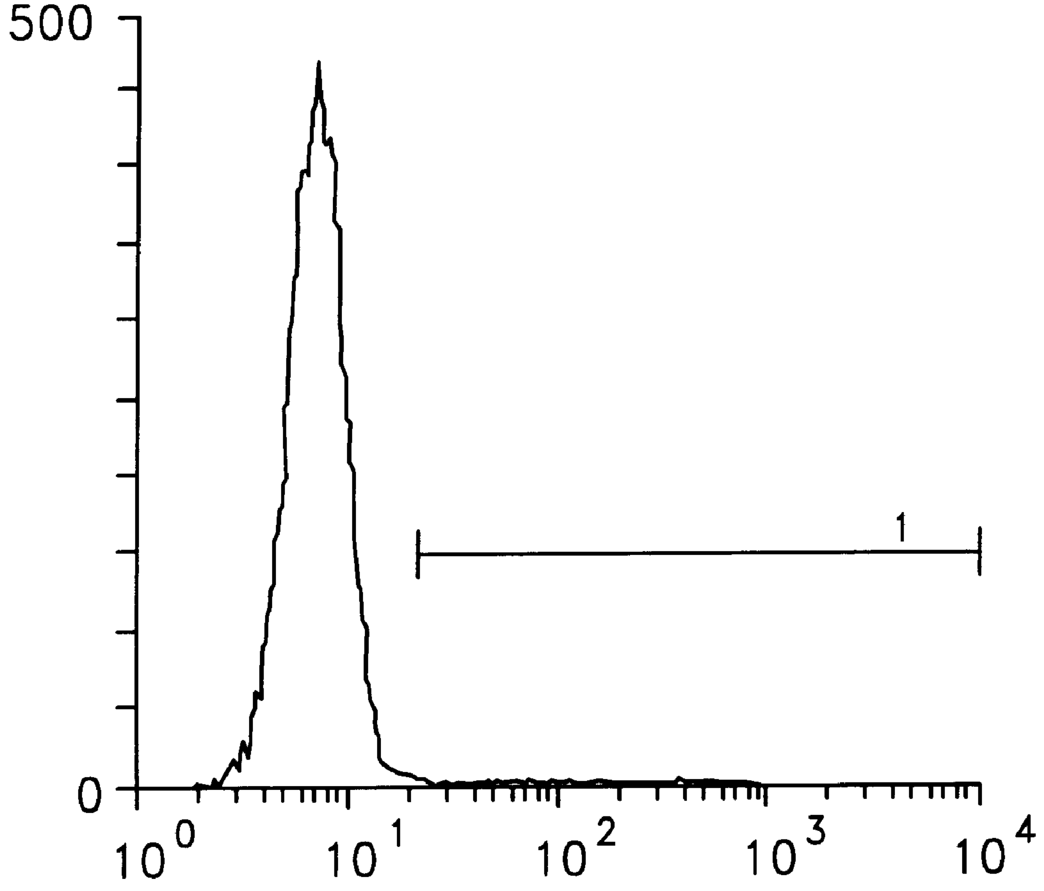
FIGS. 1A–1D show the results of a FACS sort. The horizontal axes represents fluorescence intensity while the vertical axes represents cell number. The antibodies used in the experiments summarized in FIGS. 1A–1D were a control mouse IgG, anti-gp120 monoclonal antibody 110.4, anti-gp120 monoclonal antibody D34 and anti-gp41 monoclonal antibody D6, respectively.

We have discovered that recombinant HIV-1 env proteins can be produced and purified in such a way that the humoral immune response to these immunogens exhibits a bias toward conformation-sensitive epitopes, thereby producing conformation-dependent antibodies to these proteins.

Significantly, sera from HIV-1 infected individuals is also known to contain high titers of neutralizing antibodies that are reactive against conformation sensitive epitopes. Our discovery therefore provides a means by which immunization with an env subunit preparation can be used to recapitulate some aspects of the immune response that are observed in individuals who have been infected with viable HIV-1.

The recombinant env glycoprotein that provided the advantageous immune response was modified in two ways. First, the proteolytic cleavage recognition site that ordinarily facilitates separation of the gp120 and gp41 subunits was eliminated by site directed mutagenesis. This mutation ensured that a single glycoprotein species was produced that exhibited structural features of both gp120 and gp41. Furthermore, the presence of gp41 amino acid sequences provided a means by which monomers could associate into higher order structures. The second modification to the env glycoprotein was the introduction of stop codons just upstream of the gp41 transmembrane domain. This latter modification allowed the env glycoprotein to be produced in a secreted form. Hence, the recombinant HIV-1 env immunogen described in the present invention is a secreted molecule with an amino acid sequence characteristic of both gp120 and gp41. This recombinant env glycoprotein has a molecular weight of 140 kDa, and so has been termed "gp140." Several lines of evidence suggested that secreted, oligomeric gp140 would reflect the native env structure. First, the protein was efficiently secreted. Since misfolded molecules are typically retained and degraded in the endoplasmic reticulum, it was unlikely that the folded structure of gp140 was grossly aberrant. Second, gp140 efficiently bound soluble CD4 (sCD4) and the conformation-dependent anti-gp120 monoclonal antibody (MAb), F105. Since the CD4 and F105 epitopes on gp120 are discontinuous in nature, our findings indicated the gp120 portion of the molecule exhibited structural features that were characteristic of the native conformation. The strongest evidence that purified gp140 accurately reflected native env structure came from analysis of anti-gp140 antibodies. The great majority of MAbs raised against oligomeric gp140 recognized env proteins on the surface of cells chronically infected with HIV-1. More than half (79 of 138) of the MAbs that were tested recognized conformational epitopes found on either gp120 or gp41.

These findings demonstrated that an oligomeric gp140 immunogen could be used according to the methods described below to elicit antibodies against conformational epitopes on HIV-1. The large number of MAbs obtained having specificity for conformational epitopes using the process defined below indicated that oligomeric gp140 elicited a qualitatively different immune response than monomeric protein (whether native or denatured). Our findings show that it is possible to produce and purify a soluble, oligomeric form of env which reflects the native structure of the wild-type protein.

Some of the secreted oligomeric HIV-1 env proteins that were used as immunogens in our procedures were produced by exemplary recombinant vaccinia viruses, vPE12B and vCB-14. Both of these virus constructs express genes that encode mutated env glycoproteins. The protein coding sequences in these constructs were truncated after amino acid 678 (Lys), just before the transmembrane domain so as to result in 140 kDa env molecules (gp140). To prevent dissociation of gp120 from the gp41 ectodomain fragment during purification, a deletion was made in the region of the env gene that encoded the amino acids at the gp120-gp41 cleavage site. In J. Virology 65:31 (1991), Earl et al. showed that this mutation, when introduced into the full length env gene, yielded a non-cleaved form of env that efficiently folds, assembles, is transported to the plasma membrane and can bind CD4. Notably, since the ectodomain of gp41 is required for efficient oligomerization of gp160 dimers and tetramers (Earl et al., *Proc. Natl. Acad. Sci. USA* 87:648 (1990); Earl and Moss, *AIDS Res.* 9:589–594 (1993)), the oligomeric env proteins described herein must retain the essential part of the ectodomain that is responsible for interaction between monomers. Thus, it is contemplated that recombinant oligomeric env glycoproteins which retain the advantageous immunogenic properties as described herein could be created using less than the full gp41 ectodomain. The oligomeric nature of the env immunogens must be retained, however. A synthetic early/late vaccinia virus promoter was utilized to drive high levels of gene expression in the constructs described below.

Example 1 illustrates the construction of recombinant vaccinia viruses that express modified HIV-1 env glycoproteins. It should be understood that, while the following procedures employ the BH8 HIV-1 env as the source of env sequences in the construction of vectors useful for expressing modified env glycoproteins, the HIV-1 env glycoproteins modified as described in the following Example can be created using any HIV-1 env sequence. This is true for env proteins corresponding to both laboratory-adapted strains and primary isolates of HIV-1.

EXAMPLE 1

Construction of a Recombinant Vaccinia Virus for Expression of a Truncated HIV-1 env Protein Two recombinant vaccinia viruses were constructed for production of soluble, secreted, HIV-1 env glycoprotein gp140. The BH8 HIV-1 isolate (Genbank accession number K02011) was used as the source of the env gene in these constructions. Nucleotide numbers referenced below correspond to this sequence. For construction of both recombinant viruses, two translation termination codons were inserted after nucleotide 2034, just prior to the transmembrane domain of gp41 after amino acid residue 678. These mutagenesis reactions were performed using a two-step polymerase chain reaction (PCR) protocol as described by Ho, et al. in *Gene* 77:51 (1989). Numbering of amino acids started at the beginning of the open reading frame and thus includes the signal peptide. In the first step, two DNA fragments with overlapping ends were synthesized. These fragments spanned a region of the env gene from the HindIII restriction site (nucleotide 2128), through the transmembrane coding region, to the BamHI restriction site (nucleotide 2462). One fragment was generated in a PCR reaction with a first primer (a) 5'-AACAAT TACACAAGCTTAATACACTC-3' (Seq. I.D. No: 1) containing the HindIII restriction site and a second primer (b)5'-CCCCCGCGGTTATTATTTTATATACCACAGCCA ATTTGT-3' (Seq. I.D. No: 2) containing the translation termination codons. The other fragment was generated with oligonucleotide (c)5'-GTGCTAAGGATCCGTTCACTA ATCG-3' (Seq. I.D. No: 3) containing the BamHI restriction site in conjunction with (d)5'-TAATAACCGCGGGGG TTATTCATAATGATAGTAGGAGGC-3' (Seq. I.D. No: 4). These two amplified fragments were then used together in a second PCR reaction along with oligonucleotides (a) and (c), to generate a 372 base pair fragment. This fragment was digested with HindIII and BamHI and exchanged with the analogous fragment in the env gene of pSC60 (S. Chakrabarti, unpublished), a plasmid which contains the entire env gene under control of a synthetic early/late vaccinia virus promoter. The resulting plasmid, pCB-14, thus contained the env gene truncated after amino acid 678. The proteolytic cleavage sites between gp120 and gp41 were removed by restriction fragment substitution of a 575 base pair SspI—HindIII fragment between nucleotides 1553 and 2128 with the analogous fragment from the plasmid, pPE12, which has been described by Earl et al., in *J. Virology* 65:31 (1991), to generate pPE12B. The plasmid pPE12 contained the env gene from which 12 amino acids, including the primary and secondary cleavage sites, had been removed. Hence, plasmids pCB-14 and pPE12B were used to generate recombinant vaccinia viruses (vCB-14 and vPE12B) which expressed cleavable and non-cleavable secreted gp140 molecules, respectively.

Several other recombinant vaccinia viruses were also used. vPE16 has been described by Earl et al. in *J. Virology* 64:2448 (1990) and expresses wild type gp160 under control of the vaccinia virus 7.5k promoter. vSC60 expresses wild type gp160 under control of the vaccinia virus synthetic early/late promoter. vPE12 expresses a noncleavable form of gp160; vPE8 expresses gp120; and the series VPE17, vPE18, vPE20, vPE21, and vPE22 (Earl et al., *J Virology* 65:31 (1991)) express C-terminally truncated env glycoprotein molecules. vSC64 expresses a chimeric env glycoprotein molecule consisting of HIV-2 gp120 and HIV-1 gp41 (S. Chakrabarti, unpublished). vCB-5 which has been described by Broder and Berger in *J Virology* 67:913 (1993), expresses soluble CD4 (372 amino acid residues). Finally, the plasmid, pPE63, which has been described by Earl and Moss in *AIDS Res. and Hum. Retro.* 9:589 (1993) expresses a truncated env glycoprotein via the hybrid vaccinia/T7 system.

The protein made by vCB-14 infected cells was secreted in both cleaved and non-cleaved forms while that expressed by vPE12B was recovered primarily as non-cleaved gp140.

To produce oligomeric gp140 glycoproteins for use as immunogens, BS-C-1 monolayers (ATCC CCL26) were infected with vPE12B. The secreted gp140 was purified from the culture medium using a two-step procedure as described below in Example 2.

EXAMPLE 2

Purification of Secreted Recombinant HIV-1 env Glycoprotein gp140 for Immunizations Typically, 40 confluent 150 cm$^2$ flasks, containing approximately $1.5 \times 10^7$ BS-C-1 cells per flask, were infected with vPE12B at a multiplicity of infection of 10. Two hours after infection, the monolayers were washed three times with phosphate buffered saline (PBS) to remove free virus particles and then overlaid with the commercially available reduced serum media, OPTI-MEM (Gibco, Grand Island, N.Y.). After 24 to 36 hours, the medium was harvested and culture debris was removed by centrifugation for 30 minutes at 12,000 rpm. TRITON X-100 was then added to 0.5% final concentration. Glycoproteins were then purified by LENTIL LECTIN-SEPHAROSE (Pharmacia, Piscataway, N.J.) chromatography as follows: The pooled culture supernatant containing secreted gp140 was cycled continuously over a 13 cm×1 cm column overnight. The column was washed with PBS containing 10 mM Tris-HCl pH 8.0, 0.3M NaCl, 0.5% TRITON X-100 (10 column volumes) followed by PBS containing 10 mM Tris-HCl pH 8.0 (2 column volumes). Glycoproteins were eluted with 0.5M methyl alpha-D-mannopyranoside in PBS containing 10 mM Tris-HCl pH 8.0 (3 column volumes) and concentrated 20 to 30× in CENTRICON microconcentrators. This step resulted in elimination of most contaminating proteins. The concentrated material was loaded onto 5–20% sucrose gradients and centrifuged 20 hours in an SW40 rotor at 40,000 rpm, 4° C. After fractionation of the gradients, aliquots were analyzed by sodium dodecyl sulfate polyacrylamide gel electrophoresis (SDS-PAGE) followed by Western blotting using a rabbit polyclonal antisera to HIV-1 gp160 (R160) described by Willey et al., in *Virology* 184:319 (1991) and $^{125}$I-labeled protein A (Amersham). The results of the Western blot showed a band corresponding to a 140 kDa molecular weight protein. The majority of the gp140 glycoprotein was in dimeric and higher order forms. A minor peak that contained monomeric gp140 and gp120 was also obtained. Fractions containing monomeric, dimeric, and tetrameric env glycoprotein were separately pooled and concentrated.

To verify the oligomeric status of each pooled fraction, aliquots were cross-linked with 1 mM ethylene glycolbis (succinimidylsuccinate) (EGS) (Pierce, Rockford, Ill.) and analyzed by SDS-PAGE (4%) and Western blotting with R160 as described by Earl et al., in *Proc. Natl. Acad. Sci. USA* 87:648 (1990). The Western blotting results confirmed that the dimeric and tetrameric gp140 fractions were cross linked into dimers and larger forms, respectively, whereas monomeric gp140 was not cross-linked into larger molecular weight species. The gradient separations were judged to be efficient, as there was no evidence for cross contamination between the monomer, dimer and tetramer fractions. Analysis of the protein staining pattern of each sucrose gradient peak indicated that gp140 was the predominant band in all three preparations.

Example 3 illustrates how mice can be injected with the isolated gp140 glycoproteins to stimulate an anti-env immune response. Further, Example 3 describes the production of hybridomas from the spleen cells of the immunized mice.

EXAMPLE 3

Immunization of Mice and Production of Hybridomas

A.SW/SnJ mice (Jackson Laboratories, Bar Harbor, Me.) were immunized with either monomeric (2 mice), dimeric (3 mice), or tetrameric (4 mice) gp140 preparations with RIBI adjuvant (RiBi Immunochem Research Inc., Hamilton, Mont.) as recommended by the supplier. A preliminary test indicated that emulsification of the preparations in this adjuvant did not affect the oligomeric state of the env glycoprotein as shown by chemical cross-linking followed by Western blot analysis. Mice were inoculated at 3 week intervals with 15–20 μg of purified HIV-1 env glycoprotein per mouse (½ subcutaneously and ½ intraperitoneally). Serum collected from each animal after the first inoculation efficiently reacted with gp140 as assayed by immunoprecipitation. The serum was also reactive with gp160, gp120, and gp41 as assayed by Western blotting. Mice receiving monomeric and dimeric gp140 preparations were inoculated three times while mice receiving tetrameric gp140 were inoculated four times.

Three days after the final inoculation, mice were sacrificed and the spleens harvested and prepared for cell fusion using standard methods. Splenocytes were fused with Sp2/0 Agl4 myeloma cells (ATCC CRL1581) with polyethylene glycol using a modification of the method of Gefter et al., described in *Somat. Cell Genet.* 3:231 (1977). Following polyethylene glycol fusion, the cell preparations were distributed in 96-well plates at a density of $10^5$ cells per well, based on the number of Sp2/0 partner cells, and selected in Ivscove's minimal essential medium (IMEM) supplemented with hypoxanthine/aminopterin/thymidine (HAT medium), 10% FCS (Hyclone Laboratories, Hazelton, Mont.), and 100 units of IL-6 per ml (Boehringer Mannheim Biochemicals, Indianapolis, Ind.). No feeder cell cultures were employed. The medium was replaced with fresh HAT-supplemented IMEM approximately 10 days after plating.

To identify hybridomas producing MAbs that were capable of recognizing conformation-dependent epitopes, hybridoma supernatants were tested for the ability to immunoprecipitate radioiodinated, gradient purified oligomeric or monomeric gp140. Example 4 illustrates the method used to prepare the radiolabeled env reagents, and to screen the various MAbs for binding activity.

EXAMPLE 4

Screening MAbs for gp140 Oligomer Binding

Preparations of purified monomeric, dimeric, or tetrameric gp140 glycoproteins (50 μg) were labeled with $^{125}I$ by the chloramine T method using IODOBEADS (Pierce Chemical) as described by Markwell in *Anal. Biochem.* 125:427 (1982). Radiolabeled glycoproteins were separated from free iodine by passage over a G-25 Sepharose column, and stored at 4° C. Typically, 1.0 μg of gp140 contained approximately 1 to $2\times10^6$ CPM. lodination of gp140 preparations did not disrupt their oligomeric structure as determined by cross-linking with 1 mM EGS and analysis by SDS-PAGE (4%) and Western blotting.

Twelve days after plating, the supernatants from all wells containing a hybridoma colony were screened by immunoprecipitation with radioiodinated gp140 preparations. A 100 μl sample of culture supernatant was incubated with 100 μl of PBS containing 0.5% TRITON X-100, 0.5% NONIDET P-40, radioiodinated gp140 (approximately 100,000 CPM), and 4 μg of rabbit anti-mouse IgG (Calbiochem, La Jolla, Calif.) for 1 hour at room temperature in microcentrifuge tubes. The oligomeric forms of gp140 used for screening each set were the same as that used for immunization. Protein A Sepharose beads (100 μl of a 20% suspension) were then added and tubes rocked for 30 minutes. The Protein A Sepharose beads we used in our procedures were obtained from Pharmacia (catalog number 17-0780-01). The Sepharose beads were centrifuged and the pellets were washed once with PBS containing 0.5% TRITON X-100 and 0.5% NP-40. The tubes were counted in a Beckman Gamma 5500B counter. The MAb 902, which binds the V3 loop of gp120, described by Chesebro and Wehrly, in *J. Virology* 62:3779 (1988), and polyclonal rabbit antibody R160, which identifies all forms of env, were included as positive controls. Culture supernatant from an irrelevant hybridoma was included as a negative control.

The results of this screening procedure were unambiguous. Supernatants from negative wells precipitated <1000 CPM of gp140 while most positive supernatants immunoprecipitated >20,000 CPM. During the initial screening, random samples that were deemed positive were analyzed by SDS-PAGE to ensure that gp140 was indeed immunoprecipitated. No false positives were detected. Altogether, 190 hybridomas from 9 mice in 5 fusion experiments were strongly positive using this assay. Of these, 180 were still positive after expansion. Of this number, 138 were cloned by limiting dilution using standard methods. Of this number only 15 were derived from mice immunized with monomeric gp140.

Since the mice used as spleen donors for hybridoma production had been immunized with a non-cleavable, truncated form of env it was important to demonstrate that the MAbs recognized the authentic HIV-1 env molecule. To do this, approximately 90% of the MAbs were screened by FACS analysis for the ability to recognize naturally occurring env on the surface of cells chronically infected with HIV-1 IIIB. Example 5 describes the procedures that were used to carry out these tests.

EXAMPLE 5

Identification of MAbs that Recognize Native HIV-1 env

Human T cells ($1\times10^6$/50 μl) chronically infected with HIV-1 (IIIB) were incubated with the various hybridoma supernatants described above. After 30 minutes at 4° C., the cells were washed twice with PBS containing 1% bovine serum albumin, incubated with goat anti-mouse-fluorescein isotiocyanate for 30 minutes at 4° C. and then washed 2 times. The cells were resuspended in 1 ml of 4% paraformaldehyde and analyzed with a fluorescence-activated cell sorter (FACScan; Becton Dickinson).

Figure 1B:
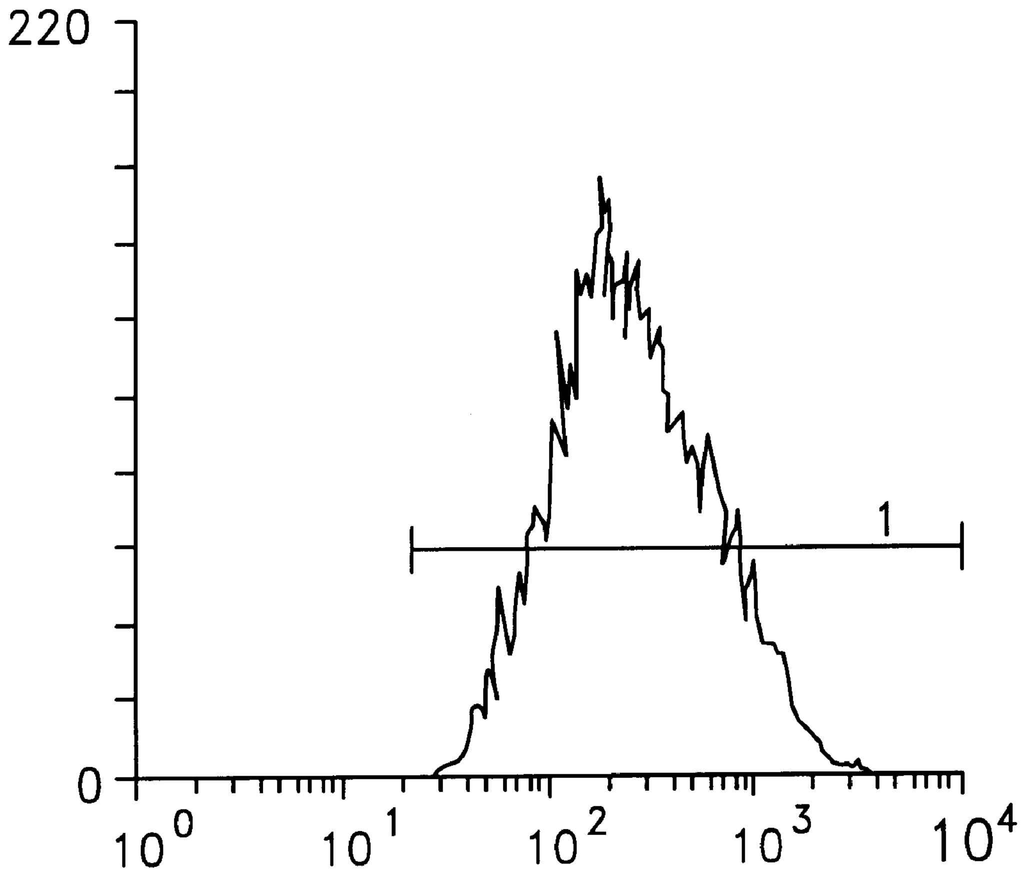
Figure 1C:
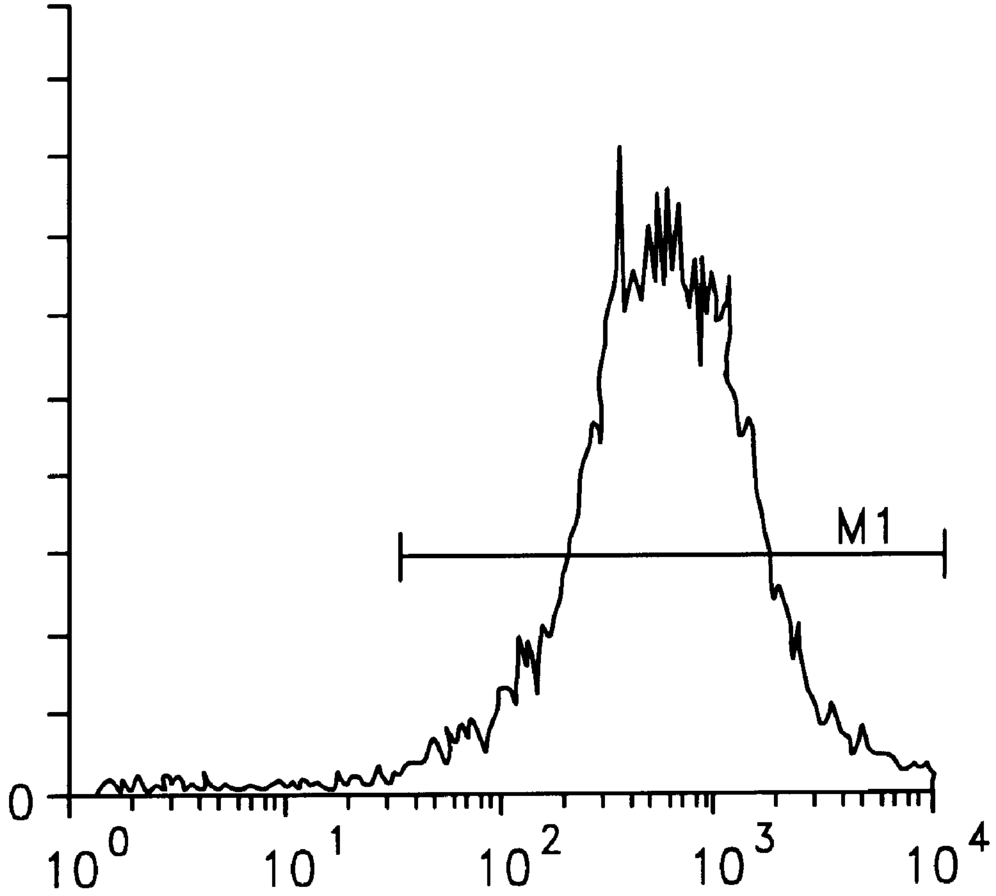
Figure 1D:
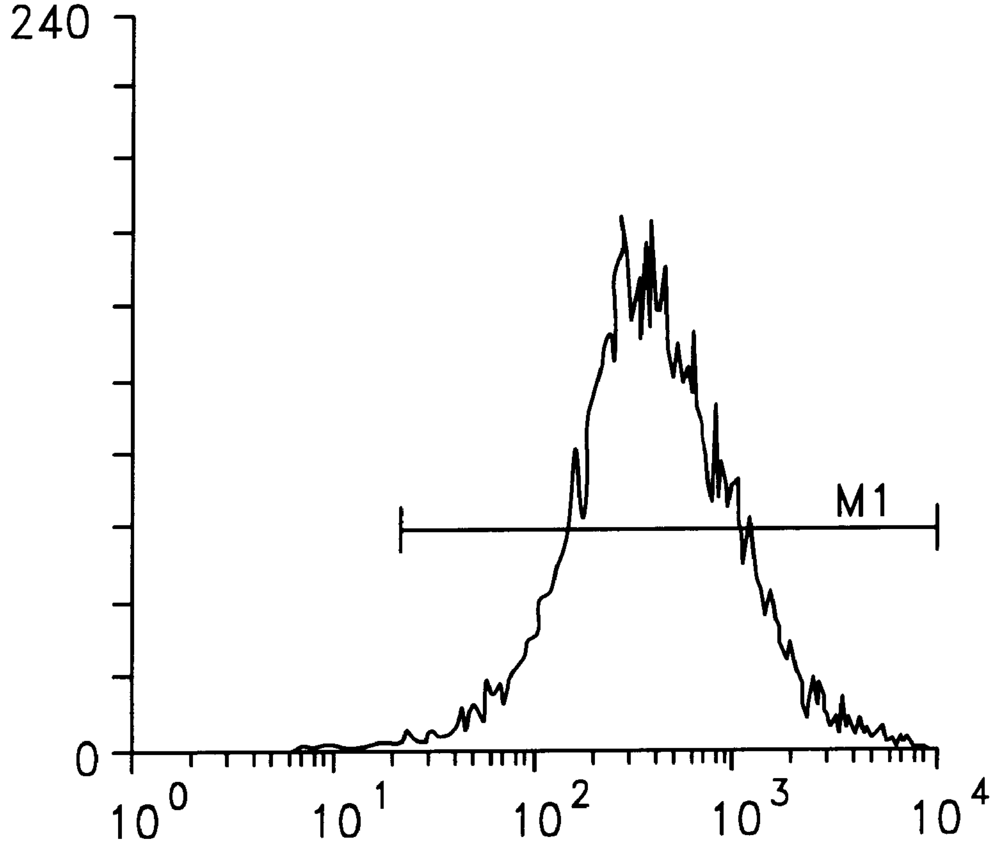

Representative FACS profiles are shown in FIGS. 1A–1D. A control mouse IgG did not label the cells (FIG. 1A), while a previously described MAb to gp120, 110.4 (FIG. 1B)

labeled the cells strongly. The profiles of one new anti-gp120 MAb, D34, and one new anti-gp41 MAb, D6 are shown in FIGS. 1C and 1D, respectively. At least 80% of the MAbs against the oligomeric form of gp140 were clearly positive in this assay. Lack of reactivity could be due to a very low titer of antibody or reactivity with an epitope that is unique to the recombinant gp140 molecule. The fact that the large majority of the MAbs tested recognized native HIV-1 env provided strong evidence that the recombinant, oligomeric gp140 used here faithfully reflected the antigenic structure of the authentic molecule.

To determine which of the MAbs recognized linear, conformation-independent epitopes, each was screened for the ability to react with Western blotted gp140 that had been denatured and reduced prior to SDS-PAGE. Monoclonal antibodies that recognized protein that had been Western blotted in this fashion were judged to bind epitopes that were independent of the protein's conformation. The methods used to make these determinations are presented in Example 6.

EXAMPLE 6

Identification of MAbs that Bind Conformation-Independent Epitopes

Protein extracts from BS-C-1 cells infected with vaccinia virus recombinants that expressed different HIV-1 env genes from Example 2 were separated on SDS-PAGE (10%) and transferred to nitrocellulose membranes. In some cases, proteins were separated on preparative gels and the nitrocellulose was cut into 10 mm strips after protein transfer. The nitrocellulose membranes were incubated with anti-gp140 monoclonal antibodies (usually 1:5 dilution) for 1 hour at room temperature. After washing with PBS containing 0.2% Tween-20, the strips were incubated with $^{125}H$ labeled rabbit anti-mouse IgG for 30 minutes followed by washing. Hybridization with polyclonal antibody R160 was done at a 1:500 dilution followed by detection with $^{125}I$ Protein A. Proteins were visualized by autoradiography using standard, well known methods.

Representative results from this Western blotting protocol are summarized in Table 1. We found that 43% of the MAbs reacted strongly with denatured env, 11% reacted very weakly (e.g., D9, D59), and 46% were completely negative even though they efficiently immunoprecipitated env. We defined MAbs that reacted either very weakly or not at all to denatured env as conformation-dependent. The remaining MAbs, which reacted strongly with denatured env, were defined as conformation-independent. By this criteria, 57% (79/138) of the MAbs recognized conformationally sensitive epitopes while 43% (59/145) recognized linear or conformation-independent epitopes (Table 2). Of the 59 conformation-independent MAbs analyzed, 50 recognized epitopes in gp120 while 9 recognized epitopes in gp41 (Table 2).

TABLE 1

Binding Specificities of Anti-gp140 MAbs

| MAb | gp160 | gp120 | gp41 |
|---|---|---|---|
| M12 | – | – | – |
| D9 | + | – | – |
| D19 | +++ | +++ | – |
| D20 | – | – | – |
| D33 | – | – | – |
| D34 | +++ | +++ | – |
| D38 | – | – | – |
| D47 | +++ | +++ | – |
| D59 | + | – | – |
| T3 | +++ | – | +++ |
| T6 | – | – | – |
| T17 | +++ | +++ | – |
| T20 | – | – | – |
| T30 | +++ | – | +++ |
| 902 | +++ | + | – |
| Negative | – | – | – |
| R160 | +++ | +++ | +++ |

Thus, the immunization and screening approach that we have described generated a large number of MAbs that bind the env glycoprotein. The procedure described in Example 6 provided results that indicated which of the subunits of the env glycoprotein harbored epitopes that were recognized by the conformation-independent antibodies. Since less than half of all the MAbs that bound the env glycoprotein recognized conformation-independent epitopes, we expected the majority of the MAbs raised against the recombinant proteins to recognize conformation-dependent epitopes.

We used a protocol based on immunoprecipitation of metabolically labeled env glycoproteins to identify which of the subunits were recognized by the conformation-dependent epitopes. Example 7 describes the techniques used to produce radiolabeled env glycoprotein reagents that were used in these assays.

EXAMPLE 7

Metabolic Labeling and Isolation of env Glycoproteins

BS-C-1 cells were infected with recombinant vaccinia virus at a multiplicity of infection of 20. At 4 hours post infection, the virus inoculum was replaced with methionine-free minimal essential medium (MEM) containing 100 $\mu$Ci [$^{35}$S]methionine/ml and incubated overnight. Cells were lysed in buffer containing 100 mM Tris-HCl pH 8.0, 100 mM NaCl, 0.5% TRITON X-100. Soluble, secreted forms of env glycoprotein were obtained from the medium of infected cells. For preparation of the ectodomain fragment of gp41 (gp41s), the medium of infected cells was concentrated using Amicon microconcentrators and separated on a 5–20% sucrose gradient as described above. Monomeric gp120 was obtained from the medium of infected cells and in some cases was purified on a sucrose density gradient.

The epitope recognized by each MAb was initially mapped to either gp120 or the gp41 ectodomain. Mapping of the conformation-independent MAbs was done by Western blot analysis as described in Example 6. Mapping of the conformation-dependent MAbs was performed by immunoprecipitation analyses using several different metabolically labeled forms of env. These included monomeric gp120; a gradient purified gp41 ectodomain fragment derived from vCB-14; and a cell lysate containing full length gp160, gp120 and gp41.

Example 8 describes the immunoprecipitation protocol that was used to identify the subunit target of MAbs that did not stain Western blotted env proteins.

EXAMPLE 8

Mapping the Subunit Targets of MAbs that Recognize Conformation-Dependent Epitopes Immunoprecipitations were performed by incubating metabolically labeled env with various antibodies overnight at 4° C. Typically, 200 μl of a hybridoma culture supernatant or 1 μl of a polyclonal antiserum were used per immunoprecipitation. Where appropriate, 4 μg of rabbit anti-mouse IgG (Calbiochem) was then added for 30 minutes followed by 100 μl of a 20% protein A SEPHAROSE suspension. After 30 minutes of rocking, the Sepharose beads were centrifuged at 1000×g for 4 minutes and the pellets were washed twice with 1 ml TRITON buffer (50 mM Tris-HCl pH 8.0, 300 mM NaCl, 0.1% TRITON X-100). Proteins were eluted by boiling 5 minutes at 100° C. in sample buffer containing 5% 2-mercaptoethanol.

Table 2 presents a summary of monoclonal antibody reactivities that were raised against native, soluble, gp140. The MAb entries in the table are classified on the basis of which subunit they recognize (gp120 or gp41), whether they recognize conformation-dependent or conformation-independent epitopes, and by the original immunogenic target oligomeric form. Of the 79 conformation-dependent MAbs analyzed, 33 mapped to gp120. Many of these anti-gp120 MAbs coprecipitated gp41 in a lysate containing gp160, gp120, and gp41 whereas none of the anti-gp41 MAbs coprecipitated gp120.

Of the MAbs that did not immunoprecipitate purified gp120, many immunoprecipitated the purified gp41 ectodomain fragment indicating that their epitopes reside in the gp41 ectodomain. However, a number of MAbs were unable to immunoprecipitate either purified gp120 or the gp41 ectodomain fragment. Some of these MAbs immunoprecipitated both gp41 and gp160 from cell lysates. As a consequence, it was not possible to determine if these MAbs recognized gp160 specific epitopes and coimmunoprecipitated gp41, or whether they recognized oligomer dependent epitopes present in gp41. To distinguish between these possibilities, the MAbs were tested for their ability to immunoprecipitate a chimeric env protein consisting of HIV-2 gp120 and HIV-1 gp41 (vSC64). The vSC64 chimeric protein is transported to the cell surface and can mediate syncytia formation, indicating that it folds and assembles correctly. None of these MAbs immunoprecipitated the HIV-2 env protein. They did, however, recognize the chimeric protein, indicating that their epitopes are present in the HIV-1 gp41 ectodomain.

Thus, more than one-third of the MAbs derived from immunization with native oligomeric gp140 were directed against epitopes in the gp41 ectodomain. Comparison of the subunit mapping results with the data on conformation dependence revealed that the antigenic structure of gp41 is exquisitely sensitive to conformation. More than 80% (43/52) of the MAbs to gp41 recognized conformation-dependent epitopes (Table 2). By contrast, the antigenic structure of gp120 appeared to be less sensitive to env tertiary structure, since 42% (33/79) of the gp120 MAbs recognized conformational epitopes (Table 2).

TABLE 2

Summary of Re-activities of MAbs Raised Against Native, Soluble, gp140

| | Total | Conf Indep Epitope | Conf Dep Epitope | V3 Loop | CD4 blocking |
|---|---|---|---|---|---|
| All Mabs | | | | | |
| Total | 138 | 59 | 79 | 15/82 | 19/76 |
| Conformation Dep | 79 | — | — | 0/32 | 19/49 |
| Conformation Indep | 59 | — | — | 15/50 | 0/27 |
| gp120 Mabs | | | | | |
| Total | 83 | 50 | 33 | 15/82 | 19/41 |
| Conformation Dep | 33 | — | — | 0/32 | 19/20 |
| Conformation Indep | 50 | — | — | 15/50 | 0/21 |
| gp41 Mabs | | | | | |
| Total | 52 | 9 | 43 | — | 0/35 |
| Conformation Dep | 43 | — | — | — | 0/29 |
| Conformation Indep | 9 | — | — | — | 0/6 |
| Immunogen-Monomer | | | | | |
| All Mabs | 15 | 9 | 6 | — | 3/12 |
| gp120 Mabs | 12 | 9 | 3 | 7/12 | 3/10 |
| gp41 Mabs | 3 | 0 | 3 | — | 0/2 |
| Immunogen-Dimer | | | | | |
| All Mabs | 68 | 19 | 49 | — | 14/41 |
| gp120 Mabs | 34 | 14 | 20 | 6/33 | 14/22 |
| gp41 Mabs | 31 | 5 | 26 | — | 0/19 |
| Immunogen-Tetramer | | | | | |
| All Mabs | 55 | 31 | 24 | — | 2/23 |
| gp120 Mabs | 37 | 27 | 10 | 2/37 | 2/9 |
| gp41 Mabs | 18 | 4 | 14 | — | 0/14 |

Example 9 describes the method used to more precisely map the env glycoprotein epitopes recognized by the MAbs. The approach we employed relied on the use of a series of recombinant env molecules that differed from each other by sequential deletions from the carboxy terminal end of the protein.

EXAMPLE 9

Detailed Epitope Mapping of MAbs

A series of C-terminally truncated env molecules expressed either by recombinant vaccinia viruses or by the transient vaccinia/T7 system described by Fuerst et al., in *Proc. Natl. Acad. Sci. USA* 83:8122 (1986), served as binding substrates for the MAbs. The env molecules used in this procedure included full length gp140 (678 amino acids), two molecules with sequential truncations in gp41 (635 and 574 amino acids), full length gp120 (502 amino acids), and three truncated forms of gp120 (393, 287, and 204 amino acids) as described by Earl et al., *J. Virology* 65:31 (1991), and by Earl et al., in *AIDS Res. and Hum. Retro.* 9:589 (1993). Mapping of the conformation-independent MAbs was performed by Western blotting extracts of cells expressing the truncated env molecules. The results are summarized in Table 3. Of the 9 anti-gp41 MAbs tested, 1 mapped to amino acids 503–574, 5 mapped to amino acids 575–635, and 3 mapped to amino acids 636–678. Of the 50 anti-gp120 MAbs to conformation-independent epitopes, 32 mapped to the amino terminal 204 amino acids, 3 mapped to amino acids 205–287, and 15 mapped to amino acids 288–393. Somewhat surprisingly, no conformation-independent MAbs mapped to the C-terminal region of gp120 (between amino acids 394–502) even though antibodies to this region are abundant in human serum. One explanation for this finding is that the C-terminal region of gp120 is partially sequestered by interactions with adjoining env subunits or with gp41.

TABLE 3

| env truncation | Total # of Mabs | Total # of amino acids |
|---|---|---|
| gp120 | | |
| 1–204 | 32 | 204 |
| 205–287 | 3 | 83 |
| 288–393 | 15 | 106 |
| 394–502 | 0 | 109 |
| gp41 | | |
| 503–574 | 1 | 72 |
| 575–635 | 5 | 61 |
| 636–678 | 3 | 43 |

Initial mapping of the conformation-dependent MAbs was done by immunoprecipitation of metabolically labeled, truncated env molecules. Of the 39 anti-gp41 MAbs tested, 3 efficiently immunoprecipitated the 636 amino acid env molecule indicating that amino acids 635–678 are not necessary for antibody recognition. Of the 32 anti-gp120 antibodies tested, only 2 immunoprecipitated the 393 amino acid gp120 molecule; one of these also immunoprecipitated the 287 amino acid molecule. However, the inability of a conformation-dependent MAb to immunoprecipitate a truncated form of env does not necessarily imply that its epitope lies completely or even partially within the truncated area since the overall structure of the truncated molecules may be significantly different from the native, full length protein.

To determine the fraction of MAbs directed against the gp120 V3 loop generated by immunization with oligomeric gp140, a V3 loop peptide ELISA assay was performed with both conformation-dependent and -independent anti-gp120 MAbs. Example 10 describes the method used to assess the ability of MAbs to recognize the V3 loop region of gp120.

EXAMPLE 10

Reactivity of MAbs with the V3 Loop Peptide

The HIV-1 IIIB V3-loop peptide (CNTRKSIRIQRGPGRAFVTIGK) (Seq. I.D. No: 5) (American Bio-Technologies, Cambridge, Mass.) and the HIV-1 MN V3-loop peptide (YNKRKRIHIGPGRAFYTTKNIIG) (Seq. I.D. No: 6) (NIAID, Biological Resources Branch) were used to determine the V3 loop reactivities of the MAbs. Briefly, the wells of IMMULON II 96 well assay plates were coated with 50 $\mu$l of 0.05M sodium carbonate pH 9.5, containing 0.25. $\mu$g of peptide, overnight at 4° C. Plates were washed with PBS containing 0.1% Tween 20 and blocked with a solution of proteolyzed gelatin (Boehringer Mannheim Biochemicals). Antibody binding was performed at room temperature for 1 hour. Serial dilutions were tested in duplicate. Bound MAb was detected with a peroxidase-conjugated anti-mouse IgG (Boehringer Mannheim Biochemicals) and 2,2'-Amino-di-[3-ethylbenzthiazoline sulfonate] substrate (Boehringer Mannheim Biochemicals). All MAbs exhibiting binding were reexamined on mock-coated plates, and no false positives were detected.

We found that 15 of 50 conformation-independent MAbs exhibited reactivity with the HIV-1 IIIB V3 loop peptide (Table 2). Of these, two cross-reacted with a V3 loop peptide from the MN strain.

Surprisingly, a correlation was observed between the oligomeric state of the immunogen used and the frequency with which anti-V3 loop MAbs were derived. Of the 15 MAbs derived from animals immunized with monomeric gp140, 7 were against the V3 loop. In contrast, only 6 of 32 MAbs from animals immunized with dimer and 2 of 38 immunized with tetramer bound to the V3 loop peptide (Table 2). Thus, a greater proportion of non-V3 loop MAbs was obtained when oligomeric gp140 was used as the immunogen indicating that the V3 loop may not be a predominant epitope when presented in the context of oligomeric gp140. For this reason, immunization with oligomeric gp140 may, as a consequence, generate a greater proportion of antibodies to conserved, conformational epitopes rather than to variable, linear regions of the protein.

Unlike antibodies to the V3 loop, neutralizing antibodies which block env-CD4 binding generally recognize conformationally sensitive epitopes and often recognize the env from divergent strains. We tested a large panel of MAbs to both gp120 and gp41 for the ability to block binding of sCD4 to env.

Example 11 describes the methods used to assay the abilities of different MAbs to block the env-CD4 interaction.

EXAMPLE 11

Ability of MAbs to Block env-CD4 Binding

Metabolically labeled gp140 and sCD4 were prepared from the medium of cells infected with vPE12B and vCB-5, respectively. Dimeric gp140 was purified by sucrose density gradient centrifugation as described above. 100 $\mu$l of hybridoma supernatant (MAb in excess of env) was incubated overnight at 4° C. with dimeric gp140. A small amount of sCD4 was added and incubated for 30 minutes at room temperature. Then 2 $\mu$g of rabbit anti-mouse IgG was added for 30 minutes, followed by 100 $\mu$l of Protein A Sepharose beads (20% suspension). After 30 minutes of gentle rocking, the beads were washed once with buffer containing 100 mM Tris-HCl pH 8.0, 100 mM NaCl, 0.5% TRITON X-100 and samples were analyzed by SDS-PAGE (10%). MAb F105, which blocks CD4 binding, was used as a positive control for CD4 blocking activity. The MAb F105 was obtained from the AIDS Research and Reference Program. The anti-V3 loop MAb, 902, that does not block CD4 binding was used as a negative control in these procedures.

However, we discovered that of the 20 conformation-dependent anti-gp120 MAbs tested, 19 efficiently blocked sCD4 binding (Table 2). In contrast, none of the 21 conformation-independent anti-gp120 MAbs tested blocked CD4 binding. As expected, none of the anti-gp41 MAbs blocked binding of sCD4 regardless of their conformational dependence. Thus, in this panel of MAbs, the ability to block sCD4 binding was restricted to conformation-dependent antibodies that bound gp120. We have therefore discovered that antibodies raised against the oligomeric form of gp140 provide advantages in that they can efficiently block CD4/env interactions.

It is known that conformation-dependent epitopes typically represent highly conserved structural features of proteins. For this reason MAbs raised against the oligomeric structure of env proteins should bind epitopes common to a broad spectrum of HIV-1 strains. Such a class of MAbs will be particularly useful as diagnostic reagents. Example 12 illustrates how one of ordinary skill in the art can identify conformation-dependent MAbs that recognize the env epitopes common to a variety of HIV-1 strains.

EXAMPLE 12

Identification of Conformation-Dependent MAbs that Recognize a Broad Spectrum of HIV-1 Strains Human blood samples are taken from normal donors and individuals known to be infected with HIV-1. The infected blood samples have been previously typed, either by antibody staining or nucleic acid analysis, so that the strain of HIV-1 that is the infectious agent in each sample is identified. A panel of blood specimens is then chosen that includes a normal sample to be used as a negative control, and several additional samples that collectively represent infections by a variety of different HIV- 1 strains. Aliquots of the blood samples are incubated with antibodies against oligomeric env. Methods for producing these antibodies are described in Example 3. Antibodies that are not specific for conformational epitopes are also included as controls. After incubation of approximately 30 minutes at 4° C., the cells are washed twice with PBS containing 1% bovine serum albumin, and incubated with a goat anti-mouse IgG antibody conjugated to fluorescein isothiocyanate for 30 minutes at 4° C. The cell samples are subsequently washed two additional times with PBS and then resuspended in 1 ml of 4% paraformaldehyde. These samples are then analyzed with a fluorescence-activated cell sorter (FACScan; Becton Dickinson). The fluorescence intensity observed for the normal control sample establishes the level of non-specific background labeling. In general, conformation-dependent MAbs bind to a wide range of HIV-1 strains, whereas non-conformational dependent antibodies only bind to one strain of HIV-1.

Given the identification of conformational-dependent MAbs that bind a broad range of HIV-1 strains, it then becomes advantageous to use these antibodies as reagents in immunoassays to identify HIV-1. These antibodies advantageously identify a wide range of different HIV-1 strains. Such a protocol will provide a more accurate and inexpensive HIV-1 assay. An immunoassay conducted with a single MAb detection reagent will require fewer reagents and a lesser number of control samples to ensure assay reliability. Example 13 illustrates how the MAbs identified in Example 12 can be used to identify a patient having an HIV-1 infection.

EXAMPLE 13

Assay for the Presence of HIV-1 Antigens in Serum Samples

A blood sample drawn from a patient suspected of having an HIV-1 infection is centrifuged to produce a serum supernatant. Samples of the test serum are placed in wells of a 96-well microtiter plate. Control samples of serum from uninfected (negative control), and HIV-1 (positive control) infected individuals are placed in different wells of the microtiter plate. A MAb having specificity for oligomeric gp140, and identified as recognizing a variety of HIV-1 strains, is then added to all wells that contain control or test serum samples. After incubation for 1–2 hours at 37° C., the wells are washed three times with PBS. Alkaline phosphatase-conjugated goat anti-mouse IgG is then added to each of the sample wells. The plates are incubated at 37° C. for an additional hour, washed twice with PBS and incubated with p-nitrophenyl phosphate at 0.5 mg/ml in diethanolamine as a phosphatase substrate. Absorbance readings at 410 nm are then taken for all samples. The negative control has a low absorbance reading, and establishes a background reference. The positive control has a high absorbance reading and indicates that all reagents used in the assay are performing properly. Comparison of the absorbance readings obtained for the wells having the patient's serum with those from the positive and negative controls unambiguously indicates the presence or absence of HIV-1 antigens.

The recombinant gp140 oligomers produced according to the method of the present invention could also be useful as a vaccine for the prevention of HIV-1 infection. Since oligomeric gp140 glycoproteins elicit a humoral immune response skewed toward conformation-dependent epitopes, rather than conformation-independent epitopes, it is likely that such a response will be advantageously protective against a broad range of HIV-1 strains.

Example 14 illustrates one vaccination protocol that can be used to stimulate a humoral immune response against conformation-specific epitopes on HIV-1. Those of ordinary skill in the art will recognize that other methods for performing a vaccination are well known in the art.

EXAMPLE 14

Use of Recombinant HIV-1 env Glycoproteins as Immunogens in a Vaccine

Human subjects at risk of exposure to HIV-1 are vaccinated with sucrose gradient-purified gp140 env glycoprotein oligomers that are produced in a manner detailed in Example 2. These glycoprotein preparations are dialyzed against cold isotonic saline buffer prior to being assayed for protein concentration. The dialyzed subunit proteins are diluted to a final concentration range of 10–1000 $\mu$g/ml, and administered by injection together with a pharmaceutically acceptable carrier, such as phosphate buffered saline. Injection of the glycoprotein immunogen is repeated once every 3 weeks, for a total of 4 injections. Immunizing doses of the gradient-purified env glycoprotein are determined in accordance with methods that are well known to those of ordinary skill in the art. Stimulation of an immune response in the patient is monitored by the appearance of anti-env antibodies in serum using standard techniques, such as ELISA, that are also known to those who are skilled in the art.

EXAMPLE 15

Use of Antibodies Against the Oligomeric Structure of gp140

A patient having an HIV infection is identified by standard, well known methods. Antibodies against the oligomeric form of gp140 are raised as described above. A pharmaceutically effective concentration of 1–10,000 $\mu$g/kg body weight of anti-gp140 are injected into the patient. A second (control) patient, suffering from an HIV infection, is injected with an antibody with specificity for a non-HIV epitope. After approximately 1 week, progress of the HIV infection is measured in each patient. The control patient has an increased progression of HIV infection as compared to the patient injected with the anti-gp140 antibodies.

Above there is described the construction of multiple forms of soluble, oligomeric HIV-1 env glycoprotein which reflect native env structure. More particularly, Example 1 describes the construction of two recombinant vaccinia viruses that express different forms of the truncated HIV-1 env protein. The first version of the secreted gp140 molecule was encoded by the vCB-14 recombinant virus. This first recombinant env glycoprotein was truncated just upstream of the gp41 transmembrane domain and could be proteolyzed to cleave the peptide backbone which joined the gp120 and gp41 domains of the molecule. A second version of the secreted gp140 molecule was encoded by the vPE12B recombinant virus. This second recombinant env glycoprotein also was truncated just upstream of the gp41 transmembrane domain, but additionally included a deletion that removed the primary and secondary cleavage sites. This meant that the resulting molecule could not be proteolytically processed to separate the gp120 and gp41 domains of the recombinant glycoprotein. For convenience, recombinant molecules having a mutated proteolytic processing site to prevent cleavage of the peptide backbone are referred to as "gp140." Molecules that retain the proteolytic processing site are referred to as "gp140(prime)".

The engineered env protein and the source of the env gene used to construct the vaccinia expression vector for producing recombinant protein are conveniently referred to by following the type of engineered protein (either gp140 or gp140(prime)) with the name of the HIV-1 isolate that served as the env gene donor in parentheses. Thus, "oligomeric gp140 (IIIB)" refers to the oligomeric form of gp140 wherein the env gene of HIV-1 (IIIB) was used as the source of the env-encoding polynucleotide for creating the vaccinia expression vector according to the method described in Example 1. Similarly, "oligomeric gp140(prime)(89.6)" refers to the oligomeric form of gp140(prime) wherein the env gene of HIV-1 (89.6) was used to create the expression vector. This nomenclature is useful because different expression constructs have been used to demonstrate that the methods for preparing and using the recombinant env proteins described herein can be generalized to different gp140 and gp140(prime) constructs which are based on the env sequences characteristic of different HIV-1 isolates.

It should be appreciated that several of the env glycoproteins characteristic of different HIV-1 isolates referred to herein are closely related to each other. For example, the BH8 and HXB2 isolates of HIV-1 are derived from the laboratory-adapted strain called HIV-1 (IIIB). The SF2 and MN strains are heterologous laboratory-adapted strain of the virus. Conversely, HIV-1 (89.6) is a primary isolate of the virus that was taken from a patient infected with HIV-1. Accordingly, it should also be appreciated that challenge with HXB2 following immunization with oligomeric gp140 (BH8) represents a homologous challenge because the HXB2 and BH8 viruses are closely related to each other.

Although oligomeric gp140 and gp140(prime) complexes useful as immunogens can be isolated using the two-step procedure described in Example 2, other procedures also can be used with equally good results. For example, below there is described a two-step purification method that involves the initial lentil lectin affinity purification step which is disclosed in Example 2, but that substitutes sizing column chromatography for sucrose density gradient separation as the second step in the procedure. It should be understood that sizing column chromatography also is known in the art as "gel filtration" or "gel exclusion" chromatography. In the purification procedures described below oligomeric gp140 and gp140(prime) were isolated using SUPERDEX-200 chromatography media that was purchased from Pharmacia. While the sucrose gradient purification method described in Example 2 and the sizing column chromatography method employed below both separate macromolecules based on size, we find that the chromatographic method is more convenient and gives equally good results. When the chromatographic step was employed, most of the uncleaved env glycoprotein eluted from the column in fractions containing material having molecular weights greater than 200 kDa. Although not shown below, the env proteins that eluted in these fractions were oligomeric, as judged by chemical cross-linking analyses. Polyacrylamide gel electrophoresis and protein staining confirmed that the purified protein co-migrated with high molecular weight protein present in medium from infected cells. Thus, oligomeric gp140 and gp140(prime) useful as immunogens can be prepared according to different protocols that advantageously preserve the oligomeric structure of the immunogen.

As detailed above, oligomeric gp140 was useful as an immunogen for stimulating the production of a diverse array of antibody reactivities, including antibodies specific for conformational epitopes in the native env glycoprotein. The repertoire of antibodies raised against oligomeric gp140 was qualitatively different from that previously raised against monomeric env immunogens. Accordingly, it is clear that env oligomeric structure has significant antigenic implications both in gp41 and gp120. The large number of MAbs we have generated against gp41, all of which immunoprecipitate native protein, should make it possible to construct a relatively detailed antigenic map of this subunit and to identify regions that are immunogenic, conserved and to which neutralizing antibodies are directed. These findings, coupled with observations that native gp140 elicited neutralizing antibodies more effectively than the denatured molecule, strongly argue that taking into account env oligomeric structure will be important for understanding the humoral response to HIV-1 infection and for the design of env subunit preparations which can effectively elicit broadly cross reactive, neutralizing antibodies.

The following Example describes experimental results which proved that an immunogenic composition that included oligomeric gp140 (BH8) advantageously stimulated an immune response that was protective against subsequent virus challenge. The SHIV virus used in the procedures described below is a chimeric simian/human immunodeficiency virus which closely mimics the mechanism of HIV-1 entry into host cells. This is because the chimeric SHIV includes the authentic HIV-1 env glycoprotein rather than the SIV env glycoprotein that ordinarily would characterize simian immunodeficiency virus (SIV). Chimeric SHIV viruses have been described, for example, by Reimann et al., in *J. Virol.* 70:3198 (1996) where it is shown that an env gene derived from a primary HIV-1 isolate conferred high in vivo replicative capacity in the rhesus monkey. Thus, the animal model employed in the following Example adequately represents the essential features of an experimental system for testing inhibition of HIV infection in a mammal.

Example 16 describes the methods used to demonstrate that an immunogenic composition that included an oligomeric gp140 (BH8) stimulated an immune response that was broadly protective. More particularly, a macaque model was used to test the immunogenicity and protective efficacy of oligomeric gp140.

EXAMPLE 16

Oligomeric gp140 Stimulates Protective Immunity in an Animal Model of HIV Infection The vPE12B recombinant virus was used to produce oligomeric gp140 (BH8) essentially as described in Examples 1 and 2 except that a gel filtration step was substituted for the sucrose density gradient step in the method of Example 2. Conditioned medium from infected cell cultures was cycled over a LENTIL LECTIN SEPHAROSE 4B column to immobilize glycoproteins. The column was washed first with PBS containing 20 mM Tris-HCl (pH 7.8), 0.2% TRITON X-100, and 0.3M NaCl; and then with PBS containing 20 mM Tris-HCl (pH 7.8). Column-bound glycoproteins were eluted with 0.5M alpha methyl mannose. After concentrating the eluted glycoproteins using a CENTRICON microconcentrator, oligomeric gp140 was purified using a SUPERDEX-200 column (Pharmacia) that was developed using PBS. Column fractions containing oligomeric gp140 were identified by standard spectrophotometric means, pooled and again concentrated. Purity of material contained in the samples was verified by standard protein gel electrophoresis and protein staining. These procedures resulted in substantially purified oligomeric gp140 that was useful as an immunogen.

Four macaques were immunized with oligomeric gp140 while two macaques served as unimmunized controls. The immunized macaques were each administered with 500 μl of a composition that included 300 μg of purified oligomeric gp140 dispersed in PBS and QS21 adjuvant (Aquila Biopharmaceuticals, Mass.). This immunogenic composition was administered intramuscularly at 0, 4, 8 and 24 week time points for a total of four administrations. Chimeric SIV viruses (SHIVs) described by Li et al. in *J. Virol.* 69:7061 (1995) and by Lu et al. in *J. Acquired. Immun. Defic. Synd.* 12:99 (1996) were tested in in vitro neutralization assays according to the procedure described by Montefiori et al. in *J. Clin. Micro.* 26:231 (1988) to verify that neutralizing antibodies had been produced before proceeding with the virus challenge. The SHIVs also served as challenge viruses to determine whether protective immunity had been established by immunization of the test animals with oligomeric gp140. Since the HIV-HXB2 clone is closely related to the BH8 clone upon which the oligomeric gp140 described in Example 1 was based, SHIV-HXB2 was used to test serum samples for the presence of neutralizing antibodies as described above.

Results from these procedures indicated that the immunogenic composition which included oligomeric gp140 stimulated a broadly reactive immune response that inhibited subsequent virus challenge. The results presented in Table 4 clearly show that animals administered with oligomeric gp140 had high neutralizing antibody titers against SHIV-HXB2 after the third and fourth immunizations at 2 and 6 months, respectively. Numerical values in Table 4 represent the serum dilution at which 50% duction in virus was observed.

TABLE 4

Serum Antibodies from Monkeys Immunized with gp140 (BH8) Neutralize SHIV-HXB2

| | | week | | | |
|---|---|---|---|---|---|
| | animal | 10 | 12 | 20 | 26 |
| gp140 | 17951 | 187 | 134 | <20 | 424 |
| | 18001 | 348 | 159 | 40 | 844 |
| | 18066 | 296 | 109 | <20 | 313 |
| | 18102 | 868 | 510 | 81 | 1315 |
| control | 18024 | <20 | <20 | <20 | <20 |
| | 18062 | <20 | <20 | <20 | <20 |

The results presented in Table 5 show that infectious activity of heterologous isolates HIV-1 MN, HIV-1 SF2, and HIV-1 89.6 also was neutralized by the anti-oligomeric gp140 immune response that had been stimulated in some of the animals. Numerical values in Table 5 represent the serum dilution at which 50% reduction in virus was observed, with higher values indicating a stronger neutralizing antibody response. Thus, neutralizing antibodies raised against the immunogen advantageously neutralized infection by viruses that displayed divergent env glycoproteins.

TABLE 5

Immunization with Oligomeric gp140 (BH8) Induced Cross-Reactive Neutralizing Antibodies

| | animal | SHIV-HXB2 | HIV-1 MN | HIV-1 SF2 | SHIV-89.6 |
|---|---|---|---|---|---|
| gp140 | 17951 | 424 | 22 | 48 | <10 |
| | 18001 | 844 | 23 | 44 | <10 |
| | 18066 | 313 | <10 | 19 | <10 |
| | 18102 | 1315 | 33 | 48 | 16 |
| control | 18024 | <20 | <10 | <10 | <10 |
| | 18062 | <20 | <10 | <10 | <10 |

Since neutralizing activity directed against a homologous isolate conceivably could be due to anti-V3 loop reactivity, neutralization of SHIV-HXB2 by serum was tested after absorption of V3 antibodies according to the procedure presented by Montefiori et al., in *J. Clin. Invest.* 92:840 (1993). Residual neutralizing activity represented the activity of antibodies directed to non-V3 epitopes.

The results presented in Table 6 show that substantial neutralizing activity remained after depletion of anti-V3 loop antibodies from the sera. Numerical values in the Table represent the serum dilution at which 50% reduction of virus was observed. These results contrast with findings obtained using sera from macaques immunized with monomeric gp120 where less than 5% of the neutralizing activity was due to non-V3 loop reactivity (D. Montefiori, personal communication). Thus, antibodies elicited by immunization with oligomeric gp140 advantageously exhibited cross-reactive neutralizing activity against a variety of heterologous HIV isolates.

TABLE 6

Absorption of Neutralizing Antibodies with a V3 Peptide (IIIB)

| animal | pre-absorption | post-absorption | % non-V3 |
|---|---|---|---|
| 17951 | 323 | 192 | 59 |
| 18001 | 422 | 174 | 41 |
| 18066 | 204 | 100 | 49 |
| 18102 | 1241 | 284 | 23 |

Three weeks after the fourth immunization with oligomeric gp140, all 6 macaques were challenged with 10 $TCID_{50}$ (tissue culture infective doses) of SHIV-HXB2. This amount of SHIV-HXB2 was sufficient to guarantee SHIV infection in a naive macaque. Infection was monitored by virus co-cultivation from macaque peripheral blood mononuclear cells (PBMCS) (Table 7), detection of anti-SIV gag antibodies (Table 8), RT-PCR (reverse transcriptase-primed PCR) of viral RNA in plasma samples (Table 9), and maintenance of high levels of neutralizing antibodies (Table 10). Numerical values in Table 7 are the number of $TCID_{50}/10^6$ cells as determined by limiting dilution analysis, and "n.i." means "no infection." In Table 8, "–" indicates the absence of a band on a Western blot or on a gel loaded with immunoprecipitate, "+" indicates the presence of a strong signal, and "+/–" indicates the presence of a weak signal. Numerical results in Table 9 represent viral RNA copies/ml, while "n.t." indicates a sample that was not tested. Numerical results in Table 10 represent the serum dilution at which 50% reduction in virus was observed. Both control animals exhibited high levels of neutralizing antibodies (Table 10), high levels of replicating virus, significant p27 antibody levels, viral RNA in plasma, and sustained neutralizing antibody titers. In contrast, the four immunized animals showed strong protective immunity. Two monkeys (17951 and 18102) exhibited sterilizing immunity. Very small but detectable evidence of viremia was found in the other 2 immunized animals. Monkey 18001 was determined to be infected by all criteria used, although virus load was reduced by 4 logs as measured by virus co-cultivation. Viremia in animal 18066 was even less pronounced than that in 18001, and the only indication of infection was a very small amount of virus in PBMC. There was no sign of infection by the other 3 assays. Thus, although two of the immunized monkeys showed signs of infection, the magnitude of infection was very limited and transient in nature. This indicated that administration of oligomeric gp140 provided protective immunity in controlling virus replication. Thus, an immunogenic composition that included oligomeric gp140 could stimulate protective immunity against SHIV infection, wherein the infecting virus displayed an env glycoprotein characteristic of HIV.

TABLE 7

Virus Isolation from PBMCs
$TCID_{50}/10^6$ Cells

| animal | week post challenge 2 | 3 | 4 | 6 | 8 | 10 | 12 | 14 | 18 | 22 | 26 |
|---|---|---|---|---|---|---|---|---|---|---|---|
| gp140 | | | | | | | | | | | |
| 17951 | n.i. | n.i. | n.i. | n.i. | n.i. | n.i | n.i. | n.i. | n.i. | n.i. | n.i. |
| 18001 | n.i. | 3 | n.i. | n.i. | 1 | n.i. | n.i. | n.i. | 1 | n.i. | n.i. |
| 18066 | 1 | n.i. | n.i. | n.i. | n.i. | n.i. | n.i. | n.i. | n.i. | n.i. | n.i. |
| 18102 | n.i. | n.i. | n.i. | n.i. | n.i. | n.i. | n.i. | n.i. | n.i. | n.i. | n.i. |
| control | | | | | | | | | | | |
| 18024 | 10000 | 1 | 1 | 1 | 1 | n.i. | n.i. | 1 | n.i. | n.i. | n.i. |
| 18062 | 10000 | 10 | 1 | 1 | n.i. | n.i. | n.i. | n.i. | n.i. | 1 | n.i. |

TABLE 8

Reactivity of Sera with gag Proteins
after Challenge with SHIV-HXB2-

| | Western blot HIV-2 p27 | | | Immunoprecipitation of $SIV_{239}gag$ | | | |
|---|---|---|---|---|---|---|---|
| | | week post-challenge | | | week post-challenge | | |
| animal | pre | 10 | 26 | pre | 4 | 12 | 34 |
| gp140 | | | | | | | |
| 17951 | – | – | – | – | – | – | – |
| 18001 | – | +/– | + | – | – | + | + |
| 18066 | – | – | – | – | – | – | – |
| 18102 | – | – | – | – | – | – | – |
| control | | | | | | | |
| 18024 | – | + | + | – | +/– | + | + |
| 18062 | – | + | + | – | +/– | + | + |

TABLE 9

Plasma Virus Levels in Monkeys Immunized with
gp140 (BH8) and Challenged with SHIV-HXB2

| | week post challenge | | | | |
|---|---|---|---|---|---|
| | SHIV-HXB2 ▼ | | | | |
| animal | 26 | 2 | 3 | 8 | 53 |
| gp140 | | | | | |
| 17951 | <1200 | <3000 | <1200 | <1200 | <300 |
| 18001 | <1200 | <3000 | 1600 | <1200 | <300 |
| 18066 | <1200 | <1200 | <1200 | <1200 | <300 |
| 18102 | <1200 | <1200 | <1200 | <1200 | <300 |
| control | | | | | |
| 18024 | <1200 | 94,000 | 11,000 | <1200 | <300 |
| 18062 | <1200 | n.t. | 8,600 | <1200 | <300 |

TABLE 10

Neutralizing Antibody Titers
After Challenge with SHIV-HXB2

| | week post challenge | | | | |
|---|---|---|---|---|---|
| | SHIV-HXB2 ▼ | | | | |
| animal | 26 | 4 | 6 | 10 | 26 |
| gp140 | | | | | |
| 17951 | 424 | 147 | 49 | 23 | <20 |
| 18001 | 844 | 563 | 690 | 471 | 469 |
| 18066 | 313 | 70 | 36 | 13 | <20 |
| 18102 | 1315 | 686 | 408 | 543 | 153 |
| control | | | | | |
| 18024 | <20 | 4032 | 705 | 510 | 968 |
| 18062 | <20 | <20 | 25 | 79 | 793 |

It would be expected from the results described in the foregoing Example that an oligomeric gp140 immunogen would be useful for stimulating a protective immune response against HIV challenge.

The recombinant gp140 and gp140(prime) molecules described herein are structurally unique and possess unexpected antigenic properties when compared with previously described compositions that include engineered env proteins. For example, Berman et al., in *J. Virol.* 62:3135 (1988) describe a recombinant protein that is truncated before the transmembrane domain of gp41 and that retains the gp120-gp41 proteolytic processing site, but that additionally includes replacement of 30 amino acids of the N-terminus of the mature (processed) form of gp160 with 25 amino acids of the herpes simplex virus type 1 glycoprotein D. Further, Berman et al., in *J. Virol.* 63:3489 (1989) describe a secreted protein called "sgp160" that is C-terminally truncated to remove the gp41 transmembrane domain and that harbors a deletion of the gp120-gp41 proteolytic processing site. However, the sgp160 differs structurally from gp140 described herein because the sgp16O protein has been modified to replace the N-terminal signal sequence and 12 amino acids of gp160 with the signal sequence and 9 amino acids from the mature N-terminus of HSV-1 gD (*Nature* 345:622 (1990)). Importantly, Berman et al. report in *Nature* 345:622 (1990) that an immunogenic composition that included a recombinant form of gp120 provided protective immunity against HIV-1 infection in test animals, but a composition including sgp160 was not protective. Thus, the finding that gp140 could stimulate protective immunity in a mammal was surprising in light of the findings that appear in the scientific literature.

The following Examples present results obtained using gp140(prime) as an immunogen. Although the methods used to produce and purify gp140(prime) are described above, the procedures are again presented to further illustrate how slightly different methods of purification can be used to obtain equally good results in the production and use of an immunogenic composition that includes oligomeric gp 140 (prime).

Example 17 describes the methods that were used to prepare gp140(prime) which was useful in preparing an immunogenic composition.

EXAMPLE 17

Method of Preparing gp140(prime)

Monolayers of BS-C-1 cells were washed twice with PBS and then infected with 5 plaque forming units (pfu) per cell of the gp140(prime)(89.6)-encoding clone vBD1 in OPTI-MEM (Gibco). The vBD1 construct was prepared essentially according to the method of Example 1, except that HIV-1 89.6 and not HIV-1 BH8 was used as the source of env-encoding polynucleotide sequences. After 2 hours, the monolayers were overlaid with OPTI-MEM and the infection allowed to proceed for 24–30 hours at 37° C. in a $CO_2$ incubator. The medium was removed and centrifuged at 1800× g for 20 minutes. The cleared supernatant was then centrifuged at 10000× g for 30 minutes. TRITON X-100 was added to a final concentration of 0.2% and sodium azide was added to a final concentration of 0.02%. The medium was cycled over a LENTIL LECTIN SEPHAROSE 4B column to immobilize glycoproteins. The column was washed with PBS containing 20 mM Tris-HCl (pH 7.8), 0.2% TRITON X-100, and 0.3M NaCl followed by PBS containing 20 mM Tris-HCl (pH 7.8) to remove nonspecifically bound material. Glycoproteins were then eluted with 0.5M alpha methyl mannose. After concentrating macromolecules using a CENTRICON microconcentartor, the gp140(prime) was purified over a SUPERDEX-200 column (Pharmacia) that was developed using PBS. Oligomeric gp140(prime) was removed from the sizing column in fractions containing proteins of molecular weight greater than 200 kDa. Purity of the eluted gp140(prime) was verified by electrophoresing a sample on a 10% SDS-polyacrylamide gel and staining for proteins.

The purified oligomeric gp140(prime), like oligomeric gp140, can be administered to a mammal at risk of exposure to HIV in order to stimulate protective immunity to the virus. The purified oligomeric glycoprotein can be combined with a carrier that typically will include a buffered saline solution, and which additionally may contain protein-stabilizing agents. While an immunogenic composition useful for stimulating an immune response necessarily will include oligomeric gp140 or oligomeric gp140(prime), the composition also may include an adjuvant. Preferred adjuvants include alum (such as ALHYDROGEL which is available from Superfos Biosector A/S (Vedback, Denmark)), polyphosphazene, MPL (RIBI ImmunoChem (Hamilton, Mont.)), QS-21 (Aquila Biopharmaceuticals, Mass.) and RAS3C (RIBI). The immunogenic compositions taught herein can be administered to a mammal in need thereof by intramuscular injection. Dosages used for immunization typically will range from 5–500 μg, more preferably from 10–300 μg, and most preferably 300 μg per injection. The immunogenic composition may be administered by injection at least once, and as many as five times over the course of several months in order to establish a vigorous immune response. The precise regimen for administering the immunogenic composition can be determined using procedures that will be familiar to those having ordinary skill in the art using no more than routine experimentation.

It is appreciated in the art that different isolates of HIV-1 can be characterized by different genotype classes which are referred to as "clades." This is significant because different clades tend to predominate in different geographic regions of the world. For example, HIV-1 isolates from the United States typically represent clade "B" isolates, while HIV-1 isolates from Thailand typically represent clade "E" isolates. Structural differences between the env glycoproteins of the various clade isolates typically are slight and are not believed to be significant with respect to the constructions discussed herein. Thus, it is possible to create recombinant oligomeric gp140 and gp140(prime) env glycoproteins corresponding to all of the different clade isolates using the approach described herein. The gp140(prime) molecules for the different clades will be C-terminally truncated forms of HIV-1 gp160 protein that is missing the transmembrane domain of gp41. Similarly, the gp140 molecules for the different clades will have all of the features of the gp140 (prime) molecules but additionally will harbor deletions or other substitutions of amino acids that will prevent proteolytic cleavage to separate the gp120 and gp41 domains of the molecule.

Since primary isolates of HIV-1 are known to differ significantly from laboratory-adapted strains with respect to neutralization properties (Moore et al., *J. Virol.* 69:101 (1995)), we have also produced oligomeric gp140(prime) (89.6) to complement the results obtained using the gp140 (BH8) that was prepared in Example 1. The gp140(prime) (89.6) was selected for study because the 89.6 virus clone was derived from a primary isolate of HIV-1 (Collman et al., *J. Virol.* 66:7517 (1992)) and because several well characterized SHIVs containing the 89.6 env are available for use as a challenge virus. Like the env protein of HIV-1 (IIIB), the 89.6 env protein was produced using a recombinant vaccinia virus expression vector. Analyses by polyacrylamide gel electrophoresis and protein staining of eluates from lentil lectin chromatography and size-separated material indicated that only about 30–50% of the env molecules present in the conditioned medium of cells infected with the recombinant vaccinia virus expressing gp140(prime)(89.6) were cleaved in the cell during processing. A substantial amount of uncleaved oligomeric gp140(prime) resulted. Virtually all of the protein eluted in the oligomeric fractions from the SUPERDEX-200 column was gp140(prime). The gp120 was not retained in the oligomeric complex. Oligomeric gp140(prime) was separated from the monomeric forms of gp140(prime)(89.6) and gp120 (89.6) by SUPERDEX-200 chromatography.

A second study using the macaque model of HIV infection described in Example 16 was conducted to verify that oligomeric gp140(prime) corresponding to an envelope other than the env of HIV-1 BH8 also could stimulate a protective immune response in a mammal. In the procedures described below macaques were immunized with oligomeric gp140(prime)(89.6) or monomeric gp120 (89.6) env protein prepared from vBD2-infected cells.

Example 18 describes the method used to immunize macaques with oligomeric gp140(prime)(89.6) or monomeric gp120 (89.6). As indicated below, both immunogenic compositions stimulated similar neutralizing antibody responses.

EXAMPLE 18

Immunization with gp140(prime)

Oligomeric gp140(prime)(89.6), prepared essentially as described in Example 17, and monomeric gp120, prepared also according to the method of Example 17 except that the monomeric gp120 fraction from the SUPERDEX-200 column was isolated and the expression vector vBD2 was used to express gp120 (89.6), were tested as immunogens essentially according to the method of Example 16.

Five animals each were immunized with one of the two immunogens. Two animals were left as unimmunized controls. The immunized monkeys received 5 administrations of the immunogenic composition that included 300 $\mu$g of the recombinant env glycoprotein dispersed in PBS and combined with QS21 adjuvant. Monkeys were administered by injection intramuscularly at 0, 4, 8, 24 and 58 weeks. Serum samples from all monkeys were tested for the presence of antibodies having neutralizing activity against SHIV-89.6, a chimeric virus containing the homologous env, according to the method of Montefiori et al. in *J. Clin. Micro.* 26:231 (1988).

The results presented in Table 11 showed that all animals administered with the oligomeric gp140(prime)(89.6) immunogen had measurable neutralizing antibodies against SHIV-89.6, a chimeric virus expressing the homologous env.

TABLE 11

Immunization with gp140(prime(89.6) or gp120 (89.6) Induced Antibodies that Neutralized SHIV-89.6 Infection

| | week | | | | | |
|---|---|---|---|---|---|---|
| animal | 10 | 26 | 29 | 32 | 36 | 60 |
| | gp140(prime) | | | | | |
| 18010 | 29 | 116 | 70 | 46 | 33 | <20 |
| 18014 | 598 | 2673 | 623 | 513 | 197 | 662 |
| 18049 | 49 | 76 | 60 | 53 | 44 | 48 |
| 18085 | 42 | 249 | 157 | 86 | 44 | 24 |
| 18135 | 31 | 40 | 52 | 55 | 27 | 31 |
| gp120 | | | | | | |
| 17983 | 27 | 57 | 58 | 43 | 29 | 33 |
| 18068 | 70 | 474 | 161 | 123 | 55 | 127 |
| 18103 | 404 | 2511 | 418 | 176 | 107 | 555 |
| 18228 | 301 | 234 | 199 | 181 | 124 | 109 |
| 18236 | 46 | 281 | 826 | 234 | 123 | 106 |
| control | | | | | | |
| 18061 | <10 | <10 | | | | <20 |
| 18162 | <10 | <10 | | | | <20 |

The results presented in Table 12 indicated that immunization with the oligomeric gp140(prime)(89.6) stimulated an immune response characterized by the production of antibodies that neutralized heterologous HIV-1 isolates, HIV-MN but not HIV-SF2. Conversely, immunization with the monomeric gp120 (89.6) stimulated production of antibodies that neutralized both HIV-MN and HIV-SF2. Numerical results in Table 9 indicate the serum dilution at which 50% of virus was neutralized.

TABLE 12

Neutralizing Antibodies Induced by Immunization with gp140(prime)(89.6) or gp120 (89.6)

| | animal | HIV-1 MN | HIV-1 SF-2 |
|---|---|---|---|
| gp140 | 18010 | 228 | <20 |
| | 18014 | >2560 | <20 |
| | 18049 | 32 | <20 |
| | 18085 | 341 | <20 |
| | 18135 | 53 | <20 |
| gp120 | 17983 | 64 | <20 |
| | 18068 | 634 | 126 |
| | 18103 | 171 | 184 |
| | 18228 | 407 | 91 |
| | 18236 | 198 | 131 |
| control | 18061 | <20 | <20 |
| | 18162 | N.T. | <20 |

Sera from all animals contained antibodies that neutralized both SHIV-89.6 and HIV-1 89.6 in a highly stringent assay wherein virus propagation and neutralization was assayed using human PBMCs. This conclusion is based on the results presented in Table 13. Numerical results in Table 13 indicate the percent reduction in infectivity at a single serum dilution (1:5). In this assay, reduction in the amount of 80% or greater was considered significant.

TABLE 13

Neutralization of Viruses Grown and Assayed in Human PBMC

| | animal | SHIV-89.6 | HIV-1 89.6 |
|---|---|---|---|
| gp140 | 18010 | 91 | 69 |
| | 18014 | 95 | 88 |
| | 18049 | 87 | 56 |
| | 18085 | 83 | 69 |
| | 18135 | 61 | 60 |
| gp120 | 17983 | 40 | 40 |
| | 18068 | 87 | 72 |
| | 18103 | 87 | 75 |
| | 18228 | 69 | 73 |
| | 18236 | 68 | 60 |
| control | 18061 | −7 | −29 |
| | 18162 | −27 | −44 |

In addition, the importance of anti-V3 loop antibodies in neutralization was studied using two chimeric viruses in which the V3 loops of HXB2 and 89.6 were exchanged (Kim et al., *J. Virol.* 69:1755 (1995)) (Table 14). Very little cross neutralization of SHIV-HXB2, containing the heterologous env, was observed. Also, no neutralization of the chimeric virus, HXΔBM, which contains the backbone of HXB2 and the V3 loop of 89.6, was detected. In contrast, neutralization of the chimeric virus 89.6ΔBM, which contains the backbone of 89.6 and V3 loop of HXB2, was observed. Taken together, this suggests that the neutralizing activity elicited by immunization with 89.6 env is not V3 specific.

This contrasts with results obtained by immunization with IIIB env in which most neutralizing activity is attributable to V3 antibodies.

TABLE 14

Neutralizing antibodies induced by immunization with 89.6 env

| animal | SHIV-89.6 | SHIV-HXB2 | HXΔBM (89.6 V3) | 89.6ΔBM (HXB2 V3) |
|---|---|---|---|---|
| gp140 | | | | |
| 18010 | 116 | 14 | <10 | 186 |
| 18014 | 2673 | 20 | <10 | 209 |
| 18049 | 76 | <10 | <10 | 33 |
| 18085 | 249 | <10 | <10 | 287 |
| 18135 | 40 | <10 | <10 | 26 |
| gp120 | | | | |
| 17983 | 57 | <10 | <10 | 32 |
| 18068 | 474 | 17 | <10 | 125 |
| 18103 | 2511 | 21 | <10 | 213 |
| 18228 | 234 | 18 | <10 | 874 |
| 18236 | 281 | 14 | <10 | 82 |
| control | | | | |
| 18061 | <10 | <10 | <10 | <20 |
| 18162 | <10 | <10 | <10 | <20 |

Example 19 describes a procedure that will be followed to confirm that test animals administered with an immunogenic composition that includes oligomeric gp140(prime)(89.6) stimulates an immune response that is protective against subsequent virus challenge.

EXAMPLE 19

Immunization with gp140(prime) Stimulates Protective Immunity

At 2–3 weeks after the initial administration of the immunogenic composition, all test animals described in the procedure under Example 18 are challenged with 10 $TCID_{50}$ units of SHIV-89.6. Viremia is measured according to standard procedures, such as those as described under Example 16. Results from the procedure show that control animals that were not administered with the gp140(prime)-containing immunogenic composition exhibit evidence of viremia at a time post-challenge. In contrast, animals that had been immunized with a composition that included the gp140(prime) show substantially no evidence for viremia. This result indicates that the immunogenic composition comprising gp140(prime) stimulates protective immunity in vivo.

Following proteolytic processing of the gp140(prime) glycoprotein there is produced a gp120 molecule and a noncovalently associated molecule representing the ectodomain of gp41. The resulting gp120 and gp41 ectodomain molecules can be physically separated from each other. For example, under Example 7 there is described a composition prepared from gradient purified gp41 ectodomain fragment derived from vCB-14. However, there also can exist a noncovalently associated bimolecular complex of gp120 and the ectodomain of gp41 that results from proteolytic processing of the gp140(prime) molecule. This bimolecular complex also is contemplated for use in an immunogenic composition useful for stimulating the production of conformation-dependent antibodies. As referred to below, this complex is termed the gp120/20 complex to reflect the fact that the gp41 component of the complex has a molecular weight of approximately 20 kDa.

Example 20 describes a method that can be used to prepare the gp120/20 complex.

EXAMPLE 20

Preparation of Recombinant gp120/20

Monolayers of host cells are washed twice with PBS and then infected with 5 plaque forming units (pfu) of a recombinant vaccinia virus expressing a gp140(prime) per cell in OPTI-MEM (Gibco), After 2 hours, the monolayers are overlaid with OPTI-MEM and the infection is allowed to proceed for 24–30 hours at 37° C. in a $CO_2$ incubator. The medium is removed and centrifuged at 1800× g for 20 minutes. It is then centrifuged at 10000×g for 30 minutes. TRITON X-100 is added to 0.2% and sodium azide is added to 0.02%. The medium is passed over a LENTIL LECTIN SEPHAROSE 4B column to bind glycoproteins. The column is washed with PBS containing 20 mM Tris-HCl pH 7.8, 0.2% TRITON X-100, and 0.3M NaCl followed by PBS containing 20 mM Tris-HCl (pH 7.8). Glycoproteins are then eluted with 0.5M alpha methyl mannose. After concentration, the HIV-1 envelope glycoprotein is purified through a SUPERDEX-200 column (Pharmacia). Fractions containing oligomeric protein, including cleaved yet stably associated gp120/20 molecules, are pooled and concentrated. Purity and extent of cleavage is checked by standard electrophoresis on a 10% SDS-polyacrylamide gel followed by staining with COOMASSIE BRILLIANT BLUE.

Purified oligomeric gp120/20 can be administered to a mammal at risk of exposure to HIV in order to stimulate protective immunity to the virus according to the same protocol that can be used for administering oligomeric gp140 or oligomeric gp140(prime), as described above. Thus, the gp120/20 can be combined with a carrier that typically will include a buffered saline solution, and further may be combined with an adjuvant including the adjuvants listed above. An immunogenic composition that includes gp120/20 can be administered to a mammal in need thereof by intramuscular injection. Dosages used for immunization typically will range from 5–500 μg, more preferably from 10–300 μg, and most preferably 300 μg per injection. The immunogenic composition may be administered by injection at least once, and as many as five times over the course of several months in order to establish a vigorous immune response.

The following Example describes the method used to produce and purify an oligomeric form of secreted gp140 (prime) wherein the env polypeptide sequence was derived from a primary isolate of HIV-1. In this Example the CM235 clade E isolate served as a template for producing the recombinant env expression vector. The recombinant glycoprotein useful as an immunogen was called gp140(prime) (CM235).

EXAMPLE 21

Method of Producing gp140(prime)(CM235)

The CM235 HIV-1 isolate (Genbank accession number L03698) was used as a source of the env-encoding polynucleotide in the construction of the gp140(prime)(CM235) expression vector. A two-step cloning procedure was used to insert the env gene into the vaccinia virus expression vector called pVOTE.2 (Ward et al. *Proc. Natl. Acad. Sci. USA* 92:6773 (1995)). In the first step, the 5' end of the gene was modified such that the ATG translation initiation codon was included in an NdeI site. This was performed by replacing an EcoRI-BalI fragment in the original polynucleotide with a fragment that was produced by annealing complementary oligonucleotides having the sequences:

5'-AATTCGCGCCATATGAGAGTAAAGGAGACACAG ATGAATTGG-3' (SEQ ID NO:7) and 5'-CCAATT CATCTGTGTCTCCTTTACTTCATATGGCGCG-3' (SEQ ID NO:8). In the second step of the cloning procedure, a translation stop codon was inserted just upstream of the region encoding the gp41 transmembrane domain. Thus, a fragment was generated in polymerase chain reaction using a plasmid containing the entire env sequence of CM235 as a template and the following two oligonucleotides as primers: 5'-CAGCATCTGTTGCAACTCACAGTCTGGGGC-3' (SEQ ID NO:9) and 5'-CGCGGCTTGGTCGACGCCTTA TTTTATATACCACAGCCACTTTGTTATGTC AAACC-3' (SEQ ID NO:10).

The amplified fragment was cut with restriction endonucleases Avr2 and SalI and then used to replace the Avr2-SalI fragment in the plasmid containing the env gene. Subsequently, the modified CM235 env gene (containing an Nde1 site at the 5' end and a SalI site at the newly created 3' end) was cloned into the pVOTE.2 vector that has been described by Ward et al., in *Proc. Natl. Acad. Sci. USA* 92:6773 (1995). The resulting plasmid, called pWS1, was used to generate the recombinant vaccinia virus called vWS1 according to standard procedures that will be familiar to those having ordinary skill in the art (see Earl and Moss (1991) p.16.17.1–16.17.16 In *Current Protocols in Molecular Biology,* Ausubel et al., eds., John Wiley & Sons, New York). Accordingly, there was created a vaccinia expression vector that encoded gp140(prime)(CM235).

Oligomeric gp140(prime)(CM235) was prepared using the vWSl expression vector according to the method of Example 17 with slight modification. According to this modification, at two hours after infecting BS-C-1 monolayers with the recombinant virus the OPTI-MEM medium that was overlaid onto the infected monolayers was made 60 mM isopropyl β-D-thiogalactopyranoside (IPTG). Procedures for preparing gp140(prime)(CM235) were otherwise as described in Example 17 and resulted in a preparation that could be used as an immunogenic composition.

Example 22 describes the methods used to demonstrate that oligomeric gp140(prime)(CM235) stimulated an anti-HIV-1 env immune response in rabbits.

EXAMPLE 22

Immunization with gp140(prime)(CM235)

Rabbits were immunized with 100 μg of oligomeric gp140(prime)(CM235) that had been prepared as described in the preceding Example. Animals received 3 intramuscular injections of the oligomeric gp140(prime)(CM235) in one of the following adjuvant combinations: (1) MPL/QS21, (2) RAS3C, (3) polyphosphazine and (4) QS21. An additional group of rabbits received only saline as a negative control. Each group consisted of 3 rabbits. Sera from all immunized rabbits contained env-binding antibodies as judged by a standard ELISA protocol using recombinant gp160 (CM244), also representing a clade E isolate as the substrate for antibody binding. This substrate protein was produced in a baculovirus system using procedures that will be familiar to those having ordinary skill in the art. No env-binding activity was detected in serum samples from the negative control rabbits, as expected. These results indicated that specific immune responses directed against the env glycoprotein had been stimulated by immunization with oligomeric gp140(prime)(CM235), as expected. In addition, serum samples from the animals in two of the adjuvant groups (MPL/QS21 and RAS3C) were assayed for neutralizing activity against five different lade E viruses. These five viruses were: CM235, 9461, 9466, NPO3 and 42368. Table 15 summarizes results from these neutralizing assays.

TABLE 15 gp140(prime)(CM235) Stimulates a Broadly Neutralizing Immune Response

| Adjuvant | Animal | >80% Reduction of Virus |
|---|---|---|
| Saline | 1 | 0/5 |
| | 2 | 0/5 |
| | 3 | 1/5 |
| MPL/QS21 | 4 | 2/5 |
| | 5 | 4/5 |
| | 6 | 2/5 |
| RAS3C | 7 | 1/5 |
| | 8 | 2/5 |
| | 9 | 1/5 |

Numerical values in the last column of the Table represent the number of viruses (out of 5 clade E viruses tested) which showed replication reduced by at least 80% in the neutralizing assay. Sera from animals 5, 6 and 8 reduced the amount of one of the viruses in the neutralization assay by 100%. These results confirmed that an oligomeric gp140(prime) stimulated a broadly reactive immune response that was not limited to a single strain of HIV-1. We reasonably expect that animals having been immunized with oligomeric gp140 (prime)(CM235) and that show evidence for neutralizing antibodies also will show evidence for protection against virus challenge. More particularly, we contemplate that the anti-HIV-1 env immune response in animals having been administered with oligomeric gp140(prime)(CM235) will inhibit infection by a challenge virus.

Example 23 describes a method of stimulating an anti-HIV immune response in a human. Although the following Example describes the use of oligomeric gp140(prime) (89.6) as an immunogen, it is contemplated that other oligomeric gp140(prime) or oligomeric gp120/20 compositions could be substituted with good results.

EXAMPLE 23

Stimulating an Anti-HIV Response in a Human

A human patient at risk of contracting an HIV infection is first identified. A pharmaceutical composition is then obtained that includes oligomeric gp140(prime)(89.6) dispersed in saline and mixed with an adjuvant appropriate for use in humans. The gp140(prime)(89.6) is prepared essentially according to the method of Example 17. The pharmaceutical composition is then injected into the patient intramuscularly at monthly intervals over the course of four months (0, 1, 2, 3 and 4 months). A serum sample isolated from the patient's blood prior to receiving the first administration of the composition failed to show evidence for HIV neutralizing antibodies when tested essentially according to the method of Montefiori et al. in *J. Clin. Micro.* 26:231 (1988). Conversely, high titer neutralizing antibodies are measured in a serum sample isolated from the injected patient two months after the last of five intramuscular injections. This shows the immunogenic composition stimulates neutralizing antibodies in a human.

The patient, having received multiple intramuscular administrations of the immunogenic composition, is inadvertently exposed to HIV by injection with HIV-contaminated gamma globulin. A naive patient who had not been administered with the immunogenic composition also was inadvertently injected with the same amount of HIV-contaminated gamma globulin. One year following exposure to the contaminated gamma globulin, blood from the naive patient contained HIV virions as judged by standard RT-PCR analysis. Blood from the patient that had received the immunogenic composition prior to being exposed to the contaminated gamma globulin did not contain amplifiable HIV transcripts. These results indicate that the immunogenic composition stimulated a protective immune response in a human.

What is claimed is:

1. An immunogenic composition comprising a pharmaceutically acceptable carrier and a recombinant uncleaved gp140 protein retaining its oligomeric structure so as that neutralizing antibodies against conformational epitopes of HIV-1 envelope proteins found on the oligomeric structure of said gp140 are produced in an immunized human, said gp140 protein being defined as a C-terminally truncated form of HIV-1 gp160 protein that is missing the gp41 transmembrane domain.

2. The immunogenic composition of claim 1, wherein said gp140 protein is obtained by running said gp14O through lectin chromatography followed by a sizings separation.

3. The immunogenic composition of claim 1, wherein said gp140 protein is obtained by running said gp140 through affinity chromatography with elution at pH8 followed by a sizing separation.

4. The immunogenic composition of claim 1, 2, or 3, wherein said gp140 protein is further defined as missing the gp120/gp41 cleaving site.

5. The immunogenic composition of claim 1, 2, or 3 wherein said gp140 protein is further defined as retaining the gp120/pg41 cleavage site.

* * * * *